(12) United States Patent
Galley et al.

(10) Patent No.: US 7,375,099 B2
(45) Date of Patent: *May 20, 2008

(54) MALONAMIDE DERIVATIVES

(75) Inventors: Guido Galley, Rheinfelden (DE); Annick Goergler, Colmar (FR); Helmut Jacobsen, Schopfheim (DE); Eric Argirios Kitas, Aesch (CH); Jens-Uwe Peters, Grenzach-Whylen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 408 days.

This patent is subject to a terminal disclaimer.

(21) Appl. No.: 10/767,784

(22) Filed: Jan. 29, 2004

(65) Prior Publication Data

US 2004/0220222 A1    Nov. 4, 2004

(30) Foreign Application Priority Data

Feb. 4, 2003    (EP)    .................................. 03002190

(51) Int. Cl.
C07D 243/12 (2006.01)
C07D 487/00 (2006.01)
C07D 313/00 (2006.01)
A61K 31/55 (2006.01)
A61P 25/28 (2006.01)

(52) U.S. Cl. .................. 514/212.04; 514/212.07; 514/221; 514/450; 540/517; 540/522; 540/523; 549/354

(58) Field of Classification Search ................ 540/517, 540/522, 523; 549/354; 514/212.04, 212.07, 514/221, 450, 228.8, 279, 290, 305, 307; 544/63; 546/1, 26, 79, 112, 133, 139
See application file for complete search history.

(56) References Cited

U.S. PATENT DOCUMENTS 6,759,404 B2    7/2004   Olson et al.
7,160,875 B2 *  1/2007   Flohr et al. ............ 514/212.04

FOREIGN PATENT DOCUMENTS

WO    WO 93/03011 A1    2/1993
WO    WO 01/27091 A1    4/2001
WO    WO01/77086    *  10/2001
WO    WO 01/77086 A1    10/2001

OTHER PUBLICATIONS

Sisodia, S., et al., *Nature Reviews/Neuroscience*, vol. 3, Apr. 2002, pp. 281-290.
Wolfe, M. S., *Current topics in Medicinal Chem.*, 2002, vol. 2, pp. 371-383.
Tsai, J., et al., *Current Medicinal Chemistry*, 2002, vol. 9, No. 11, pp. 1087-1106.
Sambamurti, K., et al., *Drug Development Research*, vol. 56, 2002, pp. 211-227.
May, P. C., *Drug Discovery Today*, vol. 6, No. 9, May 2001, pp. 459-462.
Nunan, J. et al., *FEBS Letters*, vol. 483, 2000, pp. 6-10.
Hardy, J. et al., *Science*, vol. 297, Jul. 19, 2002, pp. 353-356.
Wolfe, M. S., *Journ. Of Medicinal Chemistry*, vol. 44, No. 13, 2001, pp. 2039-2060.
Li, Y. et al., *PNAS*, vol. 97(11), 2000, pp. 6138-6143.
Brockhaus, M. et al., *Neuro Report*, vol. 9(7), 1998, pp. 1481-1486.
H.F. Dovey et al, Journal of Neurochemistry, vol. 76, No. 1, pp. 173-181 (2001).

* cited by examiner

*Primary Examiner*—James O. Wilson
*Assistant Examiner*—Paul V. Ward
(74) *Attorney, Agent, or Firm*—George W. Johnston; Patricia S. Rocha-Tramaloni; Kimberly J. Prior

(57) ABSTRACT

The invention relates to malonamide derivatives of formula

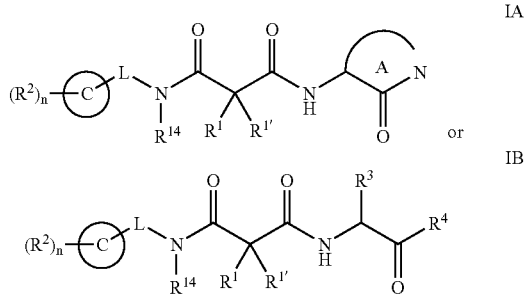

wherein each of the variables are as defined in the specification and to pharmaceutically acceptable acid addition salts thereof. The compounds are γ-secretase inhibitors. Thus, the invention also relates to pharmaceutical compositions containing these compounds and to a method of treating Alzheimer's disease by administering the compounds of the invention.

19 Claims, No Drawings

MALONAMIDE DERIVATIVES

FIELD OF THE INVENTION

The present invention relates to malonamide derivatives, pharmaceutical compositions containing these compounds, and methods of using the compounds for the treatment of Alzheimer's disease (AD). The present invention also relates to processes for manufacturing the compounds of the invention.

BACKGROUND OF THE INVENTION

Alzheimer's disease (AD) is the most common cause of dementia in later life. Pathologically AD is characterized by the deposition in the brain of amyloid in extracellular plaques and intracellular neurofibrillary tangles. The amyloid plaques are mainly composed of amyloid peptides (Abeta peptides) which originate from the β-Amyloid Precursor Protein (APP) by a series of proteolytic cleavage steps. Several forms of APP have been identified of which the most abundant are proteins of 695, 751 and 770 amino acids length. They all arise from a single gene through differential splicing. The Abeta peptides are derived from the same domain of the APP but differ at their N- and C-termini, the main species are of 40 and 42 amino-acid length.

Abeta peptides are produced from APP through the sequential action of 2 proteolytic enzymes termed β- and γ-secretase. β-Secretase cleaves first in the extracellular domain of APP just outside of the trans-membrane domain (TM) to produce a C-terminal fragment of APP containing the TM- and cytoplasmatic domain (CTFβ). CTFβ is the substrate for γ-secretase which cleaves at several adjacent positions within the TM to produce the Aβ peptides and the cytoplasmic fragment. The majority of Abeta peptides is of 40 amino acids length (Aβ40), a minor species carries 2 additional amino acids at its C-terminus. Latter is supposed to be the more pathogenic amyloid peptide.

The β-secretase is a typical aspartyl protease. The γ-secretase is a proteolytic activity consisting of several proteins, its exact composition is incompletely understood. However, the presenilins are essential components of this activity and may represent a new group of atypical aspartyl proteases which cleave within the TM of their substrates and which are themselves polytopic membrane proteins. Other essential components of γ-secretase may be nicastrin and the products of the alpha and pen-2 genes. Proven substrates for γ-secretase are the APP and the proteins of the Notch receptor family, however, γ-secretase has a loose substrate specificity and may cleave further membrane proteins unrelated to APP and Notch.

The γ-secretase activity is absolutely required for the production of Abeta peptides. This has been shown both by genetic means, i.e., ablation of the presenilin genes, and by low-molecular-weight inhibitory compounds. Since according to the amyloid hypothesis or AD the production and deposition of Abeta is the ultimate cause for the disease, it is thought that selective and potent inhibitors of γ-secretase will be useful for the prevention and treatment of AD.

Numerous documents describe the current knowledge on γ-secretase inhibition, for example the following publications:
Nature Reviews/Neuroscience, Vol. 3, April 2002/281,
Biochemical Society Transactions (2002), Vol.30. part 4,
Current Topics in Medicinal Chemistry, 2002, 2, 371-383,
Current Medicinal Chemistry, 2002, Vol. 9, No. 11, 1087-1106,
Drug Development Research, 56, 211-227, 2002,
Drug Discovery Today, Vol. 6, No. 9, May 2001, 459-462,
FEBS Letters, 483, (2000), 6-10,
Science, Vol. 297, 353-356, July 2002 and
Journ. of Medicinal Chemistry, Vol. 44, No. 13, 2001, 2039-2060.

SUMMARY OF THE INVENTION

Objects of the present invention are the compounds of formula IA or IB per se and pharmaceutically acceptable acid addition salts thereof. It has been found that the compounds of general formulas IA and IB are γ-secretase inhibitors. Therefore, objects of the invention also are pharmaceutical compositions containing compounds of formula IA or IB or their pharmaceutically acceptable acid addition salts, and use of compounds of formulas IA or IB or their pharmaceutically acceptable acid addition salts for the treatment of diseases related to γ-secretase inhibition. Another object of the invention is the use of compounds of formula IA or IB in the control and prevention of Alzheimer's disease. A further object of the invention is the manufacture of the compounds of the invention. Yet another object of the invention are all forms of optically pure enantiomers, racemates or diastereomeric mixtures for compounds of formulas IA or IB.

The invention provides malonamide derivatives of formula

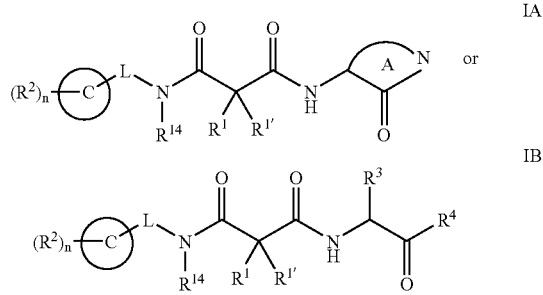

wherein

L is a bond, —(CH$_2$)$_m$—, —CH(CH$_3$)—, or is

[cyclopropyl with two F substituents] ; C is a cyclic ring, selected from the group consisting of phenyl, pyridinyl, furanyl, benzo[b]thiophenyl, tetrahydronaphthyl, indanyl, 2,2-dimethyl-[1,3]dioxolanyl and tetrahydrofuranyl;

R$^1$ and R$^{1'}$ are the same or different and are hydrogen, lower alkyl, halogen, benzyl, or lower alkenyl;

each R$^2$ is independently selected from the group consisting of hydrogen, hydroxy, halogen, lower alkyl, lower alkoxy and trifluoromethyl;

R$^3$ is phenyl or benzyl, each of which is unsubstituted or substituted by one or two substituents, selected from the group consisting of halogen or cyano, or is lower alkyl,
two hydrogen atoms,
$(CH_2)_m$—S-lower alkyl,
$(CH_2)_m$-cycloalkyl,
$(CH_2)_m$—OH,
$CH_2OCH_2$-phenyl,

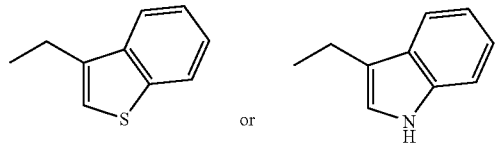

$R^4$ is lower alkoxy,
  mono-or dialkyl amino,
  $N(CH_3)(CH_2)_m$—C≡CH,
  or is a mono-, di or tricyclic group, unsubstituted or substituted by $R^5$ to $R^{10}$,
  which groups can be linked by —$N(CH_3)(CH_2)_o$- to the —C(O)-group in formula IB,

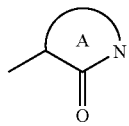

is selected from the group consisting of a)
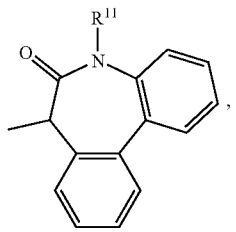

b)
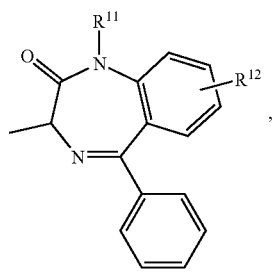

c)
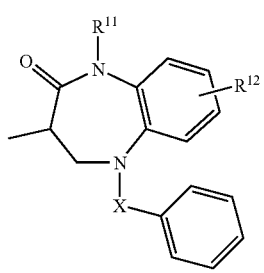

d)
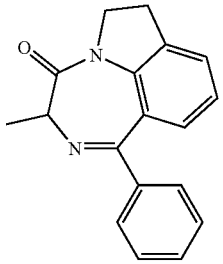

e)
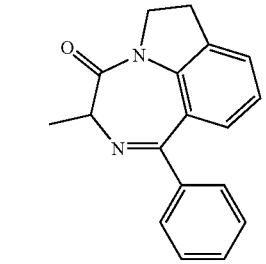

f)
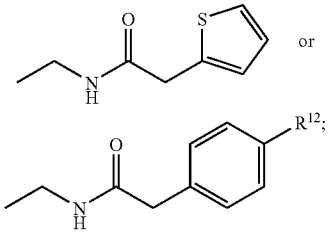

wherein
X is —$CH_2$, —$S(O)_2$ or —C(O)—;
$R^{11}$ is hydrogen or lower alkyl;
$R^{12}$ is hydrogen or halogen;
$R^{13}$ is hydrogen, CN, hydroxy, —$C(O)NH_2$,

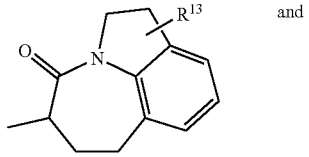

$R^{14}$ is hydrogen, lower alkyl, —$(CH_2)_2OH$ or —$(CH_2)_2CN$;
m is 1 or 2;
n is 1, 2, or 3;
o is 0, 1, or 2;
or a pharmaceutically acceptable acid addition salt thereof.

DETAILED DESCRIPTION OF THE INVENTION

The invention relates to malonamide derivatives of formula

IA
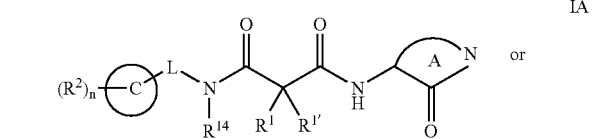

-continued

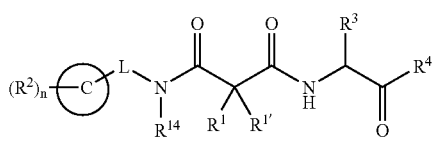
IB wherein

L is a bond, —(CH₂)ₘ—, —CH(CH₃)—, or is

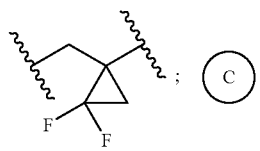
; 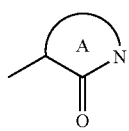

is a cyclic ring, selected from the group consisting of phenyl, pyridinyl, furanyl, benzo[b]thiophenyl, tetrahydronaphthyl, indanyl, 2,2-dimethyl-[1,3]dioxolanyl and tetrahydrofuranyl;

$R^1$ and $R^{1'}$ are the same or different and are hydrogen, lower alkyl, halogen, benzyl, or lower alkenyl;

each $R^2$ is independently selected from the group consisting of hydrogen, hydroxy, halogen, lower alkyl, lower alkoxy and trifluoromethyl;

$R^3$ is phenyl or benzyl, each of which is unsubstituted or substituted by one or two substituents, selected from the group consisting of halogen or cyano, or is lower alkyl,
two hydrogen atoms,
$(CH_2)_m$—S-lower alkyl,
$(CH_2)_m$-cycloalkyl,
$(CH_2)_m$—OH,
$CH_2OCH_2$-phenyl,

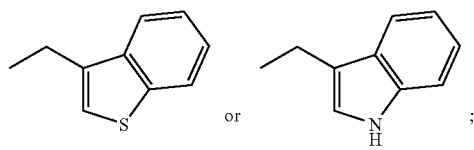

$R^4$ is lower alkoxy,
mono-or dialkyl amino,
$N(CH_3)(CH_2)_m$—C≡CH,
or is a mono-, di or tricyclic group, unsubstituted or substituted by $R^5$ to $R^{10}$,
which groups can be linked by —$N(CH_3)(CH_2)_o$- to the —C(O)-group in formula IB, is selected from the group consisting of

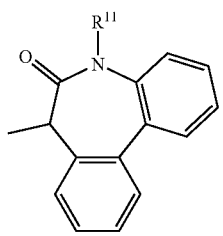
a)

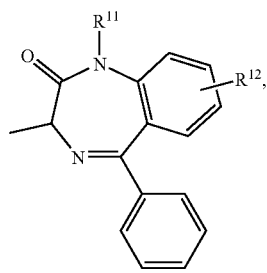
b)

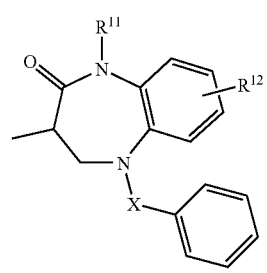
c)

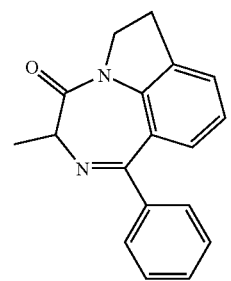
d)

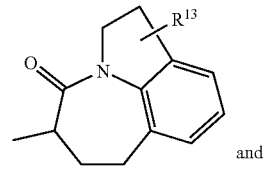
and e)

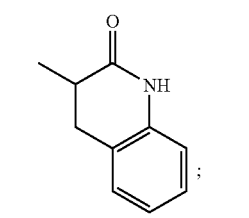
f)

wherein
X is —$CH_2$, —$S(O)_2$ or —C(O)—;
$R^{11}$ is hydrogen or lower alkyl;
$R^{12}$ is hydrogen or halogen;
$R^{13}$ is hydrogen, CN, hydroxy, —$C(O)NH_2$,

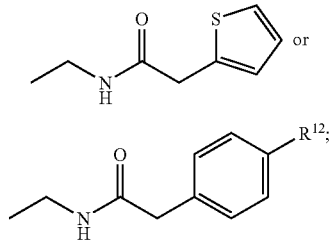

$R^{14}$ is hydrogen, lower alkyl, —$(CH_2)_2OH$ or —$(CH_2)_2CN$;

m is 1 or 2;

n is 1, 2, or 3;

o is 0, 1, or 2;

or a pharmaceutically acceptable acid addition salt thereof.

The mono-, di or tricyclic group, unsubstituted or substituted by $R^5$ to $R^{10}$, which groups can be linked by —$N(CH_3)$$(CH_2)_o$ to the —C(O)-group in formula IB, can be one of the following:

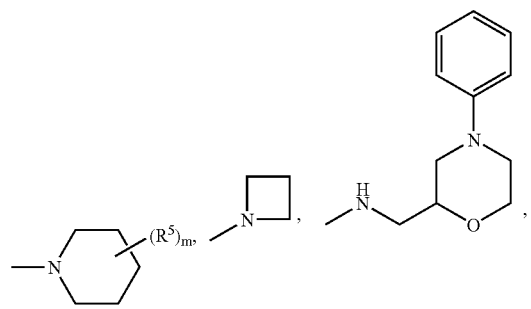

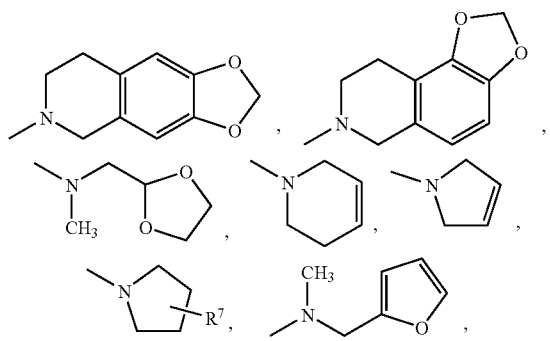

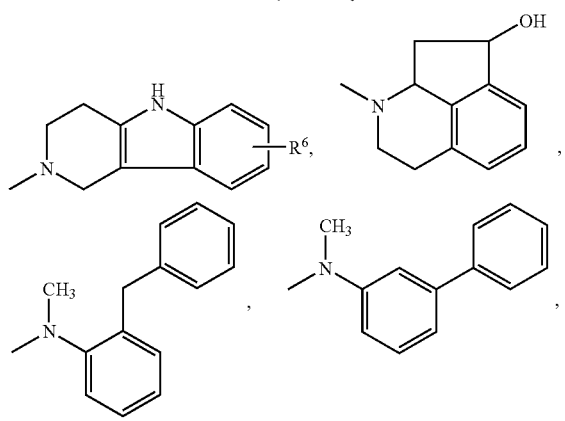

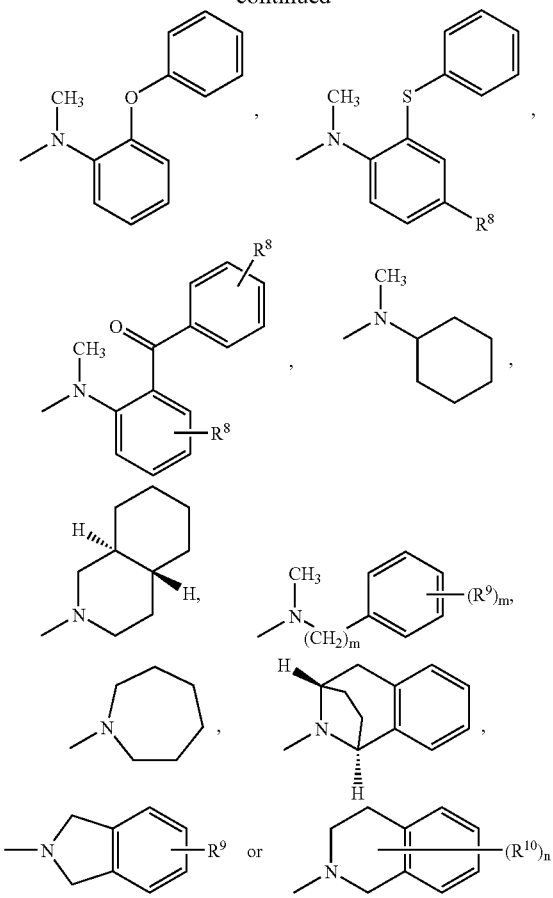

wherein
- each $R^5$ is independently selected from the group consisting of hydrogen, halogen, lower alkyl or —$(CH_2)_mOH$;
- $R^6$ is hydrogen, halogen or lower alkoxy;
- $R^7$ is hydrogen or —$CH_2OCH_3$;
- $R^8$ is hydrogen or halogen;
- $R^9$ is hydrogen, lower alkoxy, lower alkyl or amino;
- each $R^{10}$ is independently selected from the group consisting of hydrogen, lower alkyl, lower alkoxy, lower cycloalkyl, halogen, hydroxy, =O, amino, nitro, —$CH_2CN$, —$OCH_2C_6H_5$,

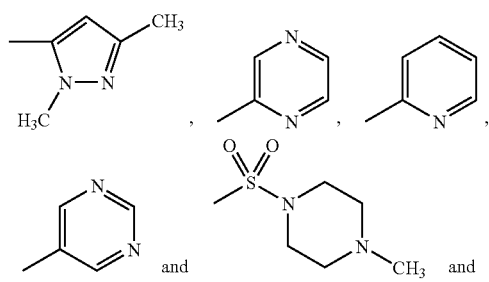

m is 1 or 2;

n is 1, 2 or 3;

As used herein, the term "lower alkyl" denotes a saturated straight- or branched-chain alkyl group containing from 1 to 6 carbon atoms, for example, methyl, ethyl, propyl, isopropyl, n-butyl, i-butyl, 2-butyl, t-butyl and the like. Preferred lower alkyl groups are groups with 1-4 carbon atoms.

The term "cycloalkyl" denotes a saturated carbocyclic group, containing 3-7 carbon atoms.

The term "halogen" denotes chlorine, iodine, fluorine and bromine.

The term "lower alkoxy" denotes a group wherein the alkyl residues is as defined above, and which is attached via an oxygen atom.

The term "lower alkenyl" denotes an unsaturated straight- or branched alkyl chain containing from 2 to 6 carbon atoms and having one or more double bonds, for example ethylene, propylene, isopropylene, and the like.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

"Therapeutically effective amount" means an amount that is effective to prevent, alleviate or ameliorate symptoms of disease or prolong the survival of the subject being treated.

In one embodiment the invention provides compounds of the general formula

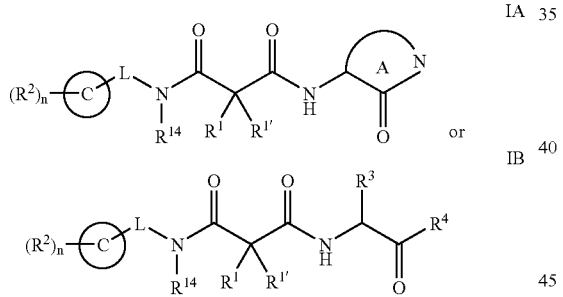

wherein
$R^1$ and $R^{1'}$ are the same or different and are hydrogen, lower alkyl, halogen, benzyl, lower alkenyl or are together with the carbon atom to which they are attached lower cycloalkyl;
each $R^2$ is independently selected from the group consisting of hydrogen, halogen, lower alkyl, lower alkoxy and trifluoromethyl;
$R^3$ is phenyl or benzyl, each of which is unsubstituted or substituted by one or two substituents, selected from the group consisting of halogen and cyano, or is
lower alkyl,
two hydrogen atoms,
$(CH_2)_m$—S-lower alkyl,
$(CH_2)_m$-cycloalkyl,
$(CH_2)_m$—OH,
$CH_2OCH_2$-phenyl,

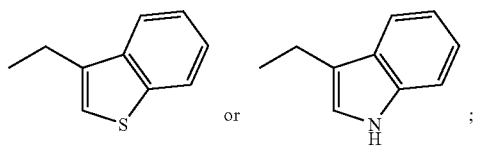

$R^4$ is lower alkoxy,
mono-or dialkyl amino,
$N(CH_3)(CH_2)_m$—C≡CH,
or is a mono-, di or tricyclic group, unsubstituted or substituted by $R^5$ to $R^{10}$, and
which groups can be linked by —N(CH$_3$)(CH$_2$)$_o$ to the —C(O)-group in formula IB, selected from the group consisting of

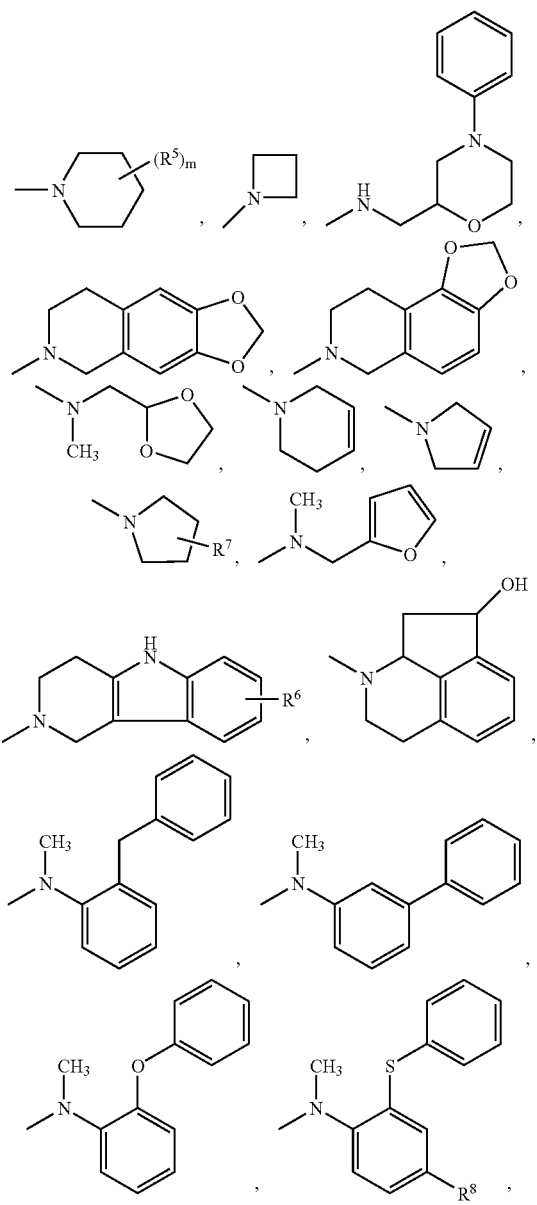

-continued

[structures shown]

wherein
each R⁵ is independently selected from the group consisting of hydrogen, halogen, lower alkyl and —(CH$_2$)$_m$OH;
R⁶ is hydrogen, halogen or lower alkoxy;
R⁷ is hydrogen or —CH$_2$OCH$_3$;
R⁸ is hydrogen or halogen;
R⁹ is hydrogen, lower alkoxy, lower alkyl or amino;
each R¹⁰ is independently selected from the group consisting of hydrogen, lower alkyl, lower alkoxy, lower cycloalkyl, halogen, hydroxy, =O, amino, nitro, —CH$_2$CN, —OCH$_2$C$_6$H$_5$,

[heterocyclic structures shown]

and m is 1 or 2;
n is 1, 2 or 3 can be one of the following rings a) [structure]

b) [structure]

c) [structure]

d) [structure]

e) [structure] and f) [structure];

wherein
X is —CH$_2$, —S(O)$_2$ or —C(O)—;
R¹¹ is hydrogen or lower alkyl;
R¹² is hydrogen or halogen;
R¹³ is hydrogen, CN, hydroxy, —C(O)NH$_2$,

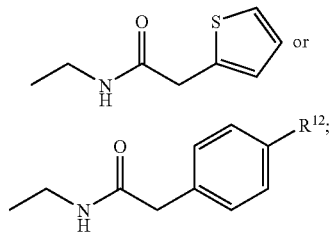

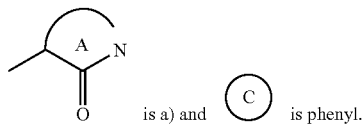

or a pharmaceutically acceptable acid addition salt thereof.

The most preferred compounds are those of formula IA, for example wherein

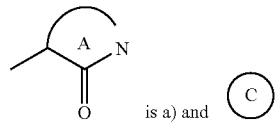  is a) and ⓒ is phenyl.

Examples of such compounds include:
N-(3,5-difluoro-benzyl)-2-methyl-N'-(5-methyl-6-oxo-6,7-dihydro-5H-dibenzo[b,d]azepin-7-yl)-malonamide,
N-(3,5-difluoro-benzyl)-2-fluoro-2-methyl-N'-(5-methyl-6-oxo-6,7-dihydro-5H-dibenzo[b,d]azepin-7-yl)-malonamide,
N-(3,5-difluoro-benzyl)-2-isopropyl-N'-(5-methyl-6-oxo-6,7-dihydro-5H-dibenzo[b,d]azepin-7-yl)-malonamide,
N-(3,5-difluoro-benzyl)-2-ethyl-N'-(5-methyl-6-oxo-6,7-dihydro-5H-dibenzo[b,d]azepin-7-yl)-malonamide,
N-(3,5-difluoro-benzyl)-2-fluoro-N'-(5-methyl-6-oxo-6,7-dihydro-5H-dibenzo[b,d]azepin-7-yl)-malonamide,
N-(3,5-difluoro-benzyl)-2,2-dimethyl-N'-(5-methyl-6-oxo-6,7-dihydro-5H-dibenzo[b,d]azepin-7-yl)-malonamide,
N-(3,5-difluoro-benzyl)-N'-(5-methyl-6-oxo-6,7-dihydro-5H-dibenzo[b,d]azepin-7-yl)-2-propyl-malonamide,
N-benzyl-2-methyl-N'-(5-methyl-6-oxo-6,7-dihydro-5H-dibenzo[b,d]azepin-7-yl)-malonamide,
N-(4-fluoro-benzyl)-2-methyl-N'-(5-methyl-6-oxo-6,7-dihydro-5H-dibenzo[b,d]azepin-7-yl)-malonamide,
N-(4-chloro-benzyl)-2-methyl-N'-(5-methyl-6-oxo-6,7-dihydro-5H-dibenzo[b,d]azepin-7-yl)-malonamide,
N-(3-fluoro-benzyl)-2-methyl-N'-(5-methyl-6-oxo-6,7-dihydro-5H-dibenzo[b,d]azepin-7-yl)-malonamide,
N-(2,5-difluoro-benzyl)-2-methyl-N'-(5-methyl-6-oxo-6,7-dihydro-5H-dibenzo[b,d]azepin-7-yl)-malonamide,
2-methyl-N-(5-methyl-6-oxo-6,7-dihydro-5H-dibenzo[b,d]azepin-7-yl)-N'-(2,3,5-trifluoro-benzyl)-malonamide,
N-(2-fluoro-benzyl)-2-methyl-N'-(5-methyl-6-oxo-6,7-dihydro-5H-dibenzo[b,d]azepin-7-yl)-malonamide,
N-(2-chloro-benzyl)-2-methyl-N'-(5-methyl-6-oxo-6,7-dihydro-5H-dibenzo[b,d]azepin-7-yl)-malonamide and
N-(3-chloro-benzyl)-2-methyl-N'-(5-methyl-6-oxo-6,7-dihydro-5H-dibenzo[b,d]azepin-7-yl)-malonamide.

Preferred compounds are further those of formula IA, wherein

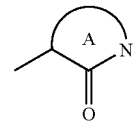 is a) and ⓒ is a cyclic ring, selected from the group consisting of furanyl, benzo[b]thiophenyl or indanyl, for example the following specific compounds:
N-furan-2-ylmethyl-2-methyl-N'-(5-methyl-6-oxo-6,7-dihydro-5H-dibenzo[b,d]azepin-7-yl)-malonamide,
N-benzo[b]thiophen-3-ylmethyl-2-methyl-N'-(5-methyl-6-oxo-6,7-dihydro-5H-dibenzo[b,d]azepin-7-yl)-malonamide and
N-(4,6-difluoro-indan-1-yl)-2-methyl-N'-(5-methyl-6-oxo-6,7-dihydro-5H-dibenzo[b,d]azepin-7-yl)-malonamide.

Further preferred compounds are those of formula IA, wherein

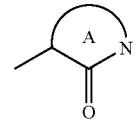

is b); for example the following compounds:
(N-(3,5-difluoro-benzyl)-2-methyl-N'-(1-methyl-2-oxo-5-phenyl-2,3-dihydro-1H-benzo[e][1,4]diazepin-3-yl)-malonamide,
N-(3,5-difluoro-benzyl)-2-fluoro-2-methyl-N'-(1-methyl-2-oxo-5-phenyl-2,3-dihydro-1H-benzo[e][1,4]diazepin-3-yl)-malonamide,
N-(3,5-difluoro-benzyl)-N'-(1-methyl-2-oxo-5-phenyl-2,3-dihydro-1H-benzo[e][1,4]diazepin-3-yl)-2-propyl-malonamide,
N-(3,5-difluoro-benzyl)-2-ethyl-N'-(1-methyl-2-oxo-5-phenyl-2,3-dihydro-1H-benzo[e][1,4]diazepin-3-yl)-malonamide and
N-(4-chloro-benzyl)-2-methyl-N'-(1-methyl-2-oxo-5-phenyl-2,3-dihydro-1H-benzo[e][1,4]diazepin-3-yl)-malonamide.

Preferred compounds are further those of formula IA, wherein is c), for example
N-(5-benzyl-1-methyl-2-oxo-2,3,4,5-tetrahydro-1H-benzo[b][1,4]diazepin-3-yl)-N'-(3,5-difluoro-benzyl)-2-methyl-malonamide,
N-(5-benzenesulfonyl-1-methyl-2-oxo-2,3,4,5-tetrahydro-1H-benzo[b][1,4]diazepin-3-yl)-N'-(3,5-difluoro-benzyl)-2-methyl-malonamide and
N-(5-benzoyl-1-methyl-2-oxo-2,3,4,5-tetrahydro-1H-benzo[b][1,4]diazepin-3-yl)-N'-(3,5-difluoro-benzyl)-2-methyl-malonamide.

A further preferred group of compounds are those, wherein

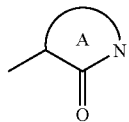

is e), for example the following compounds:
(2S-cis)-N-(3,5-difluoro-benzyl)-2-methyl-N'-{4-oxo-2-[(2-thiophen-2-yl-acetylamino)-(2R,S)-methyl]-1,2,4,5,6,7-hexahydro-azepino[3,2,1-hi]indol-5-yl}-malonamide and
(2S-cis)-N-(3,5-difluoro-benzyl)-N'-(2-{[2-(4-fluoro-phenyl)-acetylamino]-methyl}-4-oxo-1,2,4,5,6,7-hexahydro-azepino[3,2,1-hi]indol-5-yl)-2,2-dimethyl-malonamide.

Furthermore, compounds of formulas IA and IB are preferred, wherein at least one of the $R^2$ present is fluoro.

The present compounds of formulas IA and IB and their pharmaceutically acceptable acid addition salts can be prepared by methods known in the art, for example, by processes described below, which processes comprise a) reacting a compound of formula

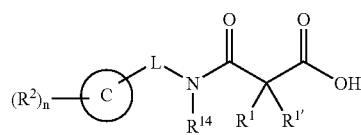  VI with a compound of formula

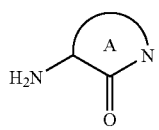  VII to produce a compound of formula

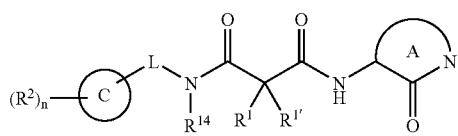  IA wherein the substituents are described above, or
b) reacting a compound of formula

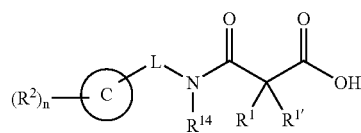  VI with a compound of formula

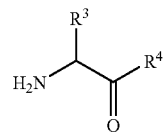  VIII to produce a compound of formula

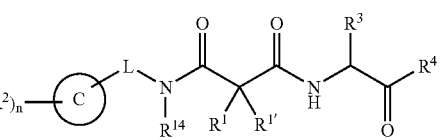  IB wherein the substituents are described above, or
c) reacting a compound of formula

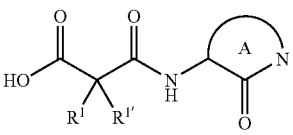  XI with a compound of formula

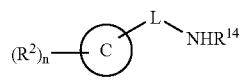  IV to produce a compound of formula

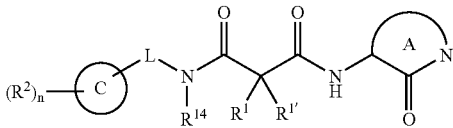  IA wherein the substituents are described above, and
if desired, converting the compounds obtained into pharmaceutically acceptable acid addition salts.

The compounds of formulas IA and IB can be prepared in accordance with the following schemes 1, 2, and 3:

Scheme 1

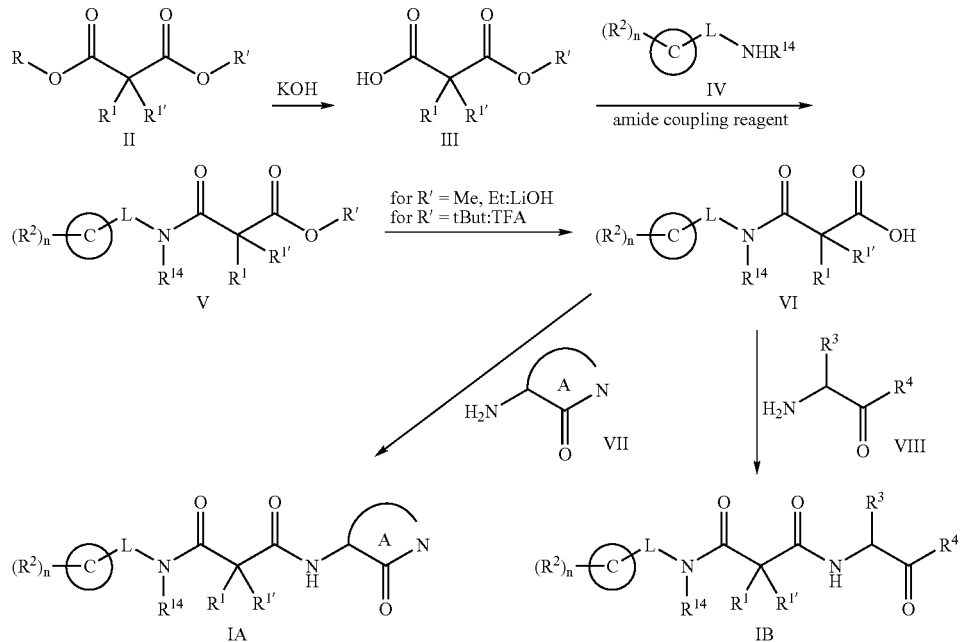

In this scheme R and R' are independently from each other lower alkyl and the other substituents are as described above.

The detailed description of the process can be found below and in Examples 1-150 and 159.

To a solution of potassium or sodium hydroxide in a solvent, such as ethanol, a methyl-malonate of formula II is added and the mixture is refluxed for about 4 hours. After cooling the reaction mixture is concentrated and dried in conventional manner and used without further purification in the next step. To a solution of the obtained methyl-malonic acid monoethyl ester (III) in tetrahydrofuran, a compound of formula IV, for example 3,5-difluorobenzylamine, N-(3-dimethylaminopropyl)-N'-ethylcarbodiimide hydrochloride, 1-hydroxybenzotrizole hydrate and N,N-diisopropyl-ethylamine are added. The mixture is stirred at room temperature for about 18 h. After concentration in vacuo HCl is added and the mixture is extracted, dried and purified as usual. To the obtained solution of a compound of formula V, water and lithium hydroxide are added and the mixture is refluxed for about 5 hours. After purification a compound of formula IA can be obtained as follows: To a solution of a compound of formula VI, for example N-(3,5-difluoro-benzyl)-2-methyl-malonamic acid in tetrahydrofuran, a compound of formula VII, N-(3-dimethylaminopropyl)-N'-ethylcarbodiimide hydrochloride, 1-hydroxybenzotrizole hydrate and N,N-diisopropyl-ethylamine are added. The mixture is stirred at room temperature for about 18 h. After concentrating, drying and purifying a compound of formula IA is obtained. A compound of formula IB can be obtained under the same conditions as described above, using a compound of formula VIII.

Scheme 2

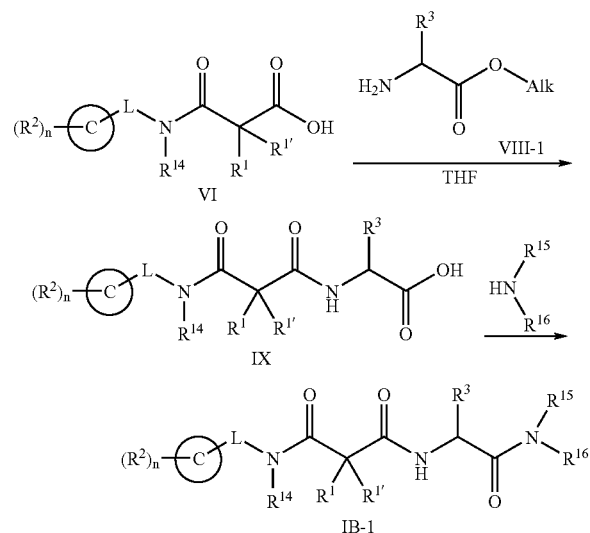

The compounds of formula IB-1 can be prepared as described in scheme 1 for the last step (VI with VII or VIII→IA or IB) if $R^4$ is lower alkoxy. The obtained acids of formula IX are placed in a disposable polypropylene tube and dissolved in DMF. TPTU (O-[2-oxo-1(2H)-pyridyl]-N,N,N',N'-tetramethyluronium-tetrafluoroborate) and a corresponding amine of formula $NHR^{15}R^{16}$ are added, and the mixture is shaken overnight at r.t.

The compounds of formula IB-1 are identical with those of formula IB, wherein $R^1$, $R^{1'}$, $R^2$ and $R^3$ are described as above and wherein $R^4$ is —$NR^{15}R^{16}$, $R^{15}$ is hydrogen or lower alkyl and $R^{16}$ is lower alkyl, —$(CH_2)_m$≡CH or —$(CH_2)_o$-mono-, di or tricyclic group, unsubstituted or substituted by $R^5$ to $R^{10}$ as described above.

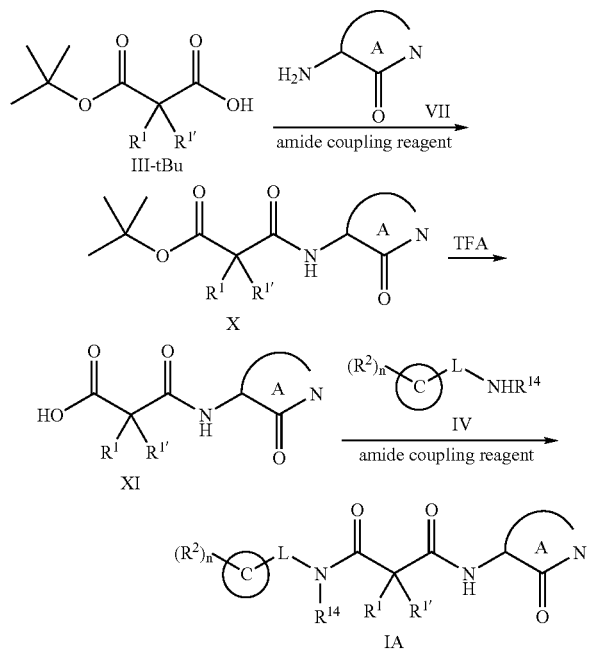

Scheme 3

The substituents are as described above.

The detailed description of the process can be found below and in Examples 151-158.

To a solution of the obtained methyl-malonic acid mono-tert-butyl ester (III-tBu) in tetrahydrofuran, a compound of formula VII, for example 7-amino-5-methyl-5H,7H-dibenzo[b,d]azepin-6-one and N-(3-dimethylaminopropyl)-N'-ethylcarbodiimide hydrochloride, 1-hydroxybenzotrizole and N,N-diisopropyl-ethylamine are added. The mixture is stirred at room temperature for about 12 h. After purification, a compound of formula X is obtained which is treated with an acid, for instance TFA, in a suitable solvent, for instance dichloromethane, to give a compound of formula XI. Using compounds of formula XI and IV, compounds of formula IA can be obtained following the amide coupling procedure described above.

Some compounds of formula IA or IB can be converted to a corresponding acid addition salt, for example, compounds containing an amine group.

The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or can be brought out of solution with a less polar solvent.

The acid addition salts of compounds of formula IA or IB can be converted to the corresponding free bases by treatment with at least a stoichiometric equivalent of a suitable base such as sodium or potassium hydroxide, potassium carbonate, sodium bicarbonate, ammonia, and the like.

The compounds of formulas IA and IB and their pharmaceutically usable acid addition salts possess valuable pharmacological properties. Specifically, it has been found that the compounds of the present invention can inhibit the γ-secretase.

The compounds were investigated in accordance with the test given hereinafter.

Description of γ-Secretase Assay

The activity of test compounds can be evaluated in assays which measure the proteolytic cleavage of suitable substrates by γ-secretase activity. These can be cellular assays where e.g., a substrate of the γ-secretase is fused in its cytoplasmic domain to a transcription factor. Cells are transfected with this fusion gene and a reporter gene, e.g., firefly luciferase, which expression is enhanced by the transcription factor. Cleavage of the fused substrate by γ-secretase will lead to expression of the reporter gene which can be monitored in appropriate assays. The γ-secretase activity can also be determined in cell-free in vitro assays where e.g., a cell lysate containing the γ-secretase complex is incubated with a suitable APP-derived substrate which is cleaved to the Abeta peptides. The amount of produced peptides can be determined with specific ELISA assays. Cell lines of neuronal origin secrete Abeta peptides which can be measured with the specific ELISA assay. Treatment with compounds which inhibit γ-secretase leads to a reduction of secreted Abeta thus providing a measure of inhibition.

The in vitro assay of γ-secretase activity uses a HEK293 membrane fraction as a source of γ-secretase and a recombinant APP substrate. Latter consist of the C-terminal 100 amino acids of human APP fused to a 6×Histidin tail for purification which is expressed in E. coli in a regulatable expression vector, e.g. pEt15. This recombinant protein corresponds to the truncated APP fragment which results after β-secretase cleavage of the extracellular domain and which constitutes the γ-secretase substrate. The assay principle is described in Li Y M et al, PNAS 97(11), 6138-6143 (2000). Hek293 cells are mechanically disrupted and the microsomal fraction is isolated by differential centrifugation. The membranes are solubilized in detergent (0.25% CHAPSO) and incubated with the APP substrate. The Abeta peptides which are produced by γ-secretase cleavage of the substrate are detected by specific ELISA assays as described (Brockhaus M et al, Neuroreport 9(7), 1481-1486 (1998)).

The preferred compounds show a $IC_{50} < 1.0$ μM. In the list below are described some data to the γ-secretase inhibition:

| Example No. | $IC_{50}$ in vitro (μM) |
|---|---|
| 8 | 0.083 |
| 2 | 0.021 |
| 12 | 0.05 |
| 13 | 0.018 |
| 14 | 0.004 |
| 16 | 0.25 |

-continued

| Example No. | IC$_{50}$ in vitro (μM) |
| --- | --- |
| 21 | 0.70 |
| 102 | 0.92 |
| 103 | 0.72 |
| 107 | 0.027 |
| 110 | 0.04 |
| 113 | 0.003 |
| 114 | 0.087 |
| 115 | 0.008 |
| 116 | 0.011 |
| 117 | 0.041 |
| 118 | 0.019 |
| 123 | 0.015 |
| 125 | 0.064 |
| 128 | 0.052 |
| 130 | 0.043 |
| 133 | 0.04 |
| 134 | 0.03 |
| 141 | 0.1 |
| 151 | 0.09 |
| 152 | 0.08 |
| 157 | 0.09 |
| 162 | 0.1 |
| 165 | 0.045 |
| 167 | 0.70 |
| 169 | 0.66 |
| 171 | 0.11 |
| 173 | 0.05 |
| 175 | 0.31 |
| 176 | 0.1 |
| 179 | 0.2 |
| 183 | 0.09 |

The present invention also provides pharmaceutical compositions containing cmpounds of formula IA or IB or a pharmaceutically acceptable acid addition salt of the compounds of formula IA or IB and a pharmaceutically acceptable carrier. Such pharmaceutical compositions can be in the form of tablets, coated tablets, dragées, hard and soft gelatine capsules, solutions, emulsions or suspensions. The pharmaceutical compositions also can be in the form of suppositories or injectable solutions. The invention further provides a process for the preparation of such compositions, which comprises bringing one or more compounds of formula IA and IB and/or a pharmaceutically acceptable acid addition salt thereof and, if desired, one or more other therapeutically valuable substances into a galenical administration form together with one or more therapeutically inert, pharmaceutically acceptable carriers.

The pharmaceutical compositions of the invention, in addition to one or more compounds of formula IA or IB, contain a pharmaceutically acceptable carrier. Suitable pharmaceutically acceptable carriers include pharmaceutically inert, inorganic or organic carriers. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

It has been found that the compounds of general formulas IA and IB are γ-secretase inhibitors. Thus, the compounds of this invention will be useful treating AD by blocking the activity of γ-secretase and reducing or preventing the formation of the various amyloidogenic Abeta peptides. In accordance with the invention compounds of formula IA and IB as well as their pharmaceutically acceptable acid addition salts are useful in the control or prevention of illnesses based on the inhibition of the γ-secretase, such as of Alzheimer's disease. In particular, the present invention provides a method for the treatment of Alzheimer's disease which comprises administering to an individual a therapeutically effective amount of a compound of the invention, for example, a compound of formula IA or IB or a pharmaceutically acceptable acid addition salt thereof.

The dosage at which the compound of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable acid addition salt thereof. The daily dosage can be administered as single dose or in divided doses and, in addition, the upper limit can also be exceeded when this is found to be indicated.

EXAMPLE 1

(N-(3,5-Difluoro-benzyl)-2-methyl-N'-(1-methyl-2-oxo-5-phenyl-2,3-dihydro-1H-benzo[e][1,4]diazepin-3-yl)-malonamide a) 2-Methyl-malonic acid monoethyl ester To a solution of 6.44 g (115 mmol) potassium hydroxide in 200 ml of ethanol 20.0 g diethyl methyl-malonate (115 mmol) was added and the mixture was refluxed for 4 hours. After cooling the reaction mixture was concentrated on a rotary evaporator, 50 ml of water was added and the mixture was extracted with ether (two times 50 ml). The aqueous solution was acidified with 4M hydrochloric acid and extracted with ethyl acetate (three times 50 ml). The combined organic layers were dried (MgSO$_4$), concentrated under reduced pressure and used without further purification.

MS m/e (%): 101.1 (M-EtO, 100), 147.1 (M+H$^+$, 8).

b) N-(3,5-Difluoro-benzyl)-2-methyl-malonamic acid ethyl ester

To a solution of 2.92 g (20 mmol) methyl-malonic acid monoethyl ester in 100 ml of tetrahydrofuran 2.86 g (20 mmol) of 3,5-difluorobenzylamine, 3.83 g (20 mmol) of N-(3-dimethylaminopropyl)-N'-ethylcarbodiimide hydrochloride, 2.70 g (20 mmol) of 1-hydroxybenzotrizole hydrate and 2.58 g (20 mmol) of N,N-diisopropyl-ethylamine were added. The mixture was stirred at room temperature for 18 h. After concentration in vacuo 0.5 N HCl (50 ml) was added and the mixture was extracted with dichloromethane (three times 50 ml). The combined organic layers were extracted with 0.5 N aqueous NaHCO$_3$ solution, dried (MgSO$_4$) and evaporated on the rotary evaporator. The residue was purified by flash chromatography (hexane/ethyl acetate=3:1) to yield 4.29 g (79%) of the tide compound as white crystalline solid.

MS m/e (%): 272.2 (M+H$^+$, 100).

c) N-(3,5-Difluoro-benzyl)-2-methyl-malonamic acid

To a solution of 4.0 g (14.75 mmol) N-(3,5-difluoro-benzyl)-2-methyl-malonamic acid ethyl ester in 300 ml of ethanol, 15 ml of water and 1.41 g (59 mmol) of lithium hydroxide were added and the mixture was refluxed for 5 hours. After concentration in vacuo water (50 ml) was added and the mixture was extracted with dichloromethane (three times 30 ml). The aqueous phase was acidified with 8 N hydrochloric acid and extracted with dichloromethane (four times 30 ml).

The combined organic layers from the second extraction were dried ($MgSO_4$) and evaporated in vacuo to yield an orange oil. The mixture was dissolved in a small amount of ethyl acetate and hexane and left overnight. The resulting white crystals were collected by filtration to give 11.4 g (74.8%) of the title compound.

MS m/e (%): 142.1 (C6H3F2-CH=$NH_2^+$, 100), 243.1 ($M+H^+$, 16).

d) (RS)-N-(3,5-Difluoro-benzyl)-2-methyl-N'-(1-methyl-2-oxo-5-phenyl-2,3-dihydro-1H-benzo[e][1,4]diazepin-3-yl)-malonamide To a solution of 0.073 g (0.3 mmol) N-(3,5-difluoro-benzyl)-2-methyl-malonamic acid in 5 ml of tetrahydrofuran 0.080 g (0.3 mmol) of (3RS)-3-amino-1,3-dihydro-1-methyl-5-phenyl-2H-1,4-benzodiazepin-2-one, 0.058 g (0.3 mmol) of N-(3-dimethylaminopropyl)-N'-ethylcarbodiimide hydrochloride, 0.040 g (0.3 mmol) of 1-hydroxybenzotrizole hydrate and 0.039 g (0.3 mmol) of N,N-diisopropyl-ethylamine were added. The mixture was stirred at room temperature for 18 h. After concentration in vacuo 0.5 N HCl (5 ml) was added and the mixture was extracted with dichloromethane (three times 5 ml). The combined organic layers were extracted with 0.5 N aqueous $NaHCO_3$ solution, dried ($MgSO_4$) and evaporated on the rotary evaporator. The residue was purified by flash chromatography (hexane/ethyl acetate=3:1) to yield 0.099 g (67%) of the diastereomeric mixture of title compound as white solid.

MS m/e (%):491.2 ($M+H^+$, 100).

EXAMPLE 2

N-(3,5-Difluoro-benzyl)-2-fluoro-2-methyl-N'-(1-methyl-2-oxo-5-phenyl-2,3-dihydro-1H-benzo[e][1,4]diazepin-3-yl)-malonamide The title compound was obtained in comparable yields according to the procedures described for example 1 using 2-fluoro-2-methyl-malonic acid diethyl ester instead of diethyl methyl-malonate in step a).

MS m/e (%): 509.3 ($M+H^+$, 100).

EXAMPLE 3

(3RS)-N-(3,5-Difluoro-benzyl)-2,2-dimethyl-N'-(1-methyl-2-oxo-5-phenyl-2,3-dihydro-1H-benzo[e][1,4]diazepin-3-yl)-malonamide The title compound was obtained in comparable yields according to the procedures described for example 1 using 2,2-dimethyl-malonic acid diethyl ester instead of diethyl methyl-malonate in step a).

MS m/e (%): 505.2 ($M+H^+$, 100).

EXAMPLE 4

(3RS)-N-(3,5-Difluoro-benzyl)-N'-(1-methyl-2-oxo-5-phenyl-2,3-dihydro-1H-benzo[e][1,4]diazepin-3-yl)-malonamide The title compound was obtained in comparable yields according to the procedures described for example 1 using diethyl malonate instead of diethyl methyl-malonate in step a).

MS m/e (%): 477.2 ($M+H^+$, 100).

EXAMPLE 5

N-(3,5-Difluoro-benzyl)-2-fluoro-2-methyl-N'-(4-oxo-1-phenyl-3,4,6,7-tetrahydro-[1,4]diazepino[6,7,1-hi]indol-3-yl)-malonamide The title compound was obtained in comparable yields according to the procedures described for example 1 using 2-fluoro-2-methyl-malonic acid diethyl ester instead of diethyl methyl-malonate in step a) and (3RS)-3-amino-1-phenyl-6,7-dihydro-3H-[1,4]diazepino[6,7,1-hi]indol-4-one instead of (3RS)-3-amino-1,3-dihydro-1-methyl-5-phenyl-2H-1,4-benzodiazepin-2-one in step d).

MS m/e (%): 521.1 ($M+H^+$, 100).

EXAMPLE 6

N-(3,5-Difluoro-benzyl)-2-methyl-N'-{(S)-phenyl-[(4-phenyl-morpholin-2-ylmethyl)-carbamoyl]-methyl}-malonamide The title compound was obtained in comparable yields according to the procedures described for example 1 using (2S)-2-amino-2-phenyl-N-((2RS)-4-phenyl-morpholin-2-ylmethyl)-acetamide instead of (3RS)-3-amino-1,3-dihydro-1-methyl-5-phenyl-2H-1,4-benzodiazepin-2-one in step d).

MS m/e (%): 551.2 ($M+H^+$, 100).

EXAMPLE 7

(2S)-2-[2-(RS)-(3,5-Difluoro-benzylcarbamoyl)-propionylamino]-phenyl-acetic acid tert-butyl ester The title compound was obtained in comparable yields according to the procedures described for example 1 using (S)-phenylglycine tert.butyl ester instead of (3RS)-3-amino-1,3-dihydro-1-methyl-5-phenyl-2H-1,4-benzodiazepin-2-one in step d).

MS m/e (%): 377.3 ($M+H^+$, 100).

EXAMPLE 8

(2RS)-N-[(1S)-1-(Cyclohexyl-methyl-carbamoyl)-1-phenyl-methyl]-N'-(3,5-difluoro-benzyl)-2-methyl-malonamide The title compound was obtained in comparable yields according to the procedures described for example 1 using (2S)-2-amino-N-cyclohexyl-N-methyl-2-phenyl-acetamide instead of (3RS)-3-amino-1,3-dihydro-1-methyl-5-phenyl-2H-1,4-benzodiazepin-2-one in step d).

MS m/e (%): 472.3 ($M+H^+$, 100).

EXAMPLE 9

(2S)-2-[(2RS)-2-(3,5-Difluoro-benzylcarbamoyl)-propionylamino]-3-phenyl-propionic acid tert-butyl ester The title compound was obtained in comparable yields according to the procedures described for example 1 using (S)-phenylalanine tert.butyl ester instead of (3RS)-3-amino-1,3-dihydro-1-methyl-5-phenyl-2H-1,4-benzodiazepin-2-one in step d).

MS m/e (%): 391.2 (M+H$^+$, 100).

EXAMPLE 10

(2S)-2-[(2RS)-2-(3,5-Difluoro-benzylcarbamoyl)-2-fluoro-propionylamino]-2-phenyl-acetic acid tert-butyl ester The title compound was obtained in comparable yields according to the procedures described for example 1 using 2-fluoro-2-methyl-malonic acid diethyl ester instead of diethyl methyl-malonate in step a) and (S)-phenylglycine tert.butyl ester instead of (3RS)-3-amino-1,3-dihydro-1-methyl-5-phenyl-2H-1,4-benzodiazepin-2-one in step d).

MS m/e (%): 473.1 (M+Na$^+$, 100), 451.0 (M+H$^+$, 29).

EXAMPLE 11

N-(3,5-Difluoro-benzyl)-2-fluoro-2-methyl-N'-(2-oxo-1,2,3,4-tetrahydro-quinolin-3-yl)-malonamide The title compound was obtained in comparable yields according to the procedures described for example 1 using 2-fluoro-2-methyl-malonic acid diethyl ester instead of diethyl methyl-malonate in step a) and (RS)-3-amino-3,4-dihydro-1H-quinolin-2-one instead of (3RS)-3-amino-1,3-dihydro-1-methyl-5-phenyl-2H-1,4-benzodiazepin-2-one in step d).

MS m/e (%): 406.4 (M+H$^+$, 100).

EXAMPLE 12

N-(5-Benzyl-1-methyl-2-oxo-2,3,4,5-tetrahydro-1H-benzo[b][1,4]diazepin-3-yl)-N'-(3,5-difluoro-benzyl)-2-methyl-malonamide a) (1-Methyl-2-oxo-2,3,4,5-tetrahydro-1H-benzo[b][1,4]diazepin-3-yl)-carbamic acid tert-butyl ester To a solution of 0.94 g (3.38 mmol) (S)-(2-oxo-2,3,4,5-tetrahydro-1H-benzo[b][1,4]diazepin-3-yl)-carbamic acid tert-butyl ester dissolved in 20 ml of tetrahydrofurane at −78° C., 3.4 ml of lithium bis(trimethylsilyl)amide (1N solution in tetrahydrofurane) were added. The reaction mixture was stirred for 30 minutes at −78° C. and was allowed to reach room temperature. Iodomethane was slowly added and stirring was continued for 2 hours. The reaction mixture was diluted with ethyl acetate, washed with saturated NaHSO$_4$ solution and separated. The aqueous phase was extracted twice with ethyl acetate (2×50 ml). The combined organic layers were washed with water (2×100 ml), with brine (1×100 ml), dried over MgSO$_4$, filtered and evaporated. The residue was purified by chromatography (heptane/ethyl acetate=7:3) to yield 0.855 g (87%) of the product as a light yellow solid.

MS m/e (%): 292.2 (M+H$^+$, 100)

b) (5-Benzyl-1-methyl-2-oxo-2,3,4,5-tetrahydro-1H-benzo[b][1,4]diazepin-3-yl)-carbamic acid tert-butyl To a solution of 0.087 g (1-methyl-2-oxo-2,3,4,5-tetrahydro-1H-benzo[b][1,4]diazepin-3-yl)-carbamic acid tert-butyl ester in 1 ml of dimethylformamide 0.138 g of potassium carbonate and 0.062 g of benzyl bromide were added. The reaction mixture was shaken for 16 hours at room temperature. The solvent was evaporated in vacuo and the residue was dissolved in ethyl acetate and washed with water. The organic layer was dried over MgSO4, filtered and evaporated. The residue was purified by chromatography (heptane/ethyl acetate=2:1) to yield 0.10 g (87%) of the product as a light yellow foam.

MS m/e (%): 382.3 (M+H$^+$, 100).

c) N-(5-Benzenesulfonyl-1-methyl-2-oxo-2,3,4,5-tetrahydro-1H-benzo[b][1,4]diazepin-3-yl)-N'-(3,5-difluoro-benzyl)-2-methyl-malonamide To a solution of 0.086 g (5-benzyl-1-methyl-2-oxo-2,3,4,5-tetrahydro-1H-benzo[b][1,4]diazepin-3-yl)-carbamic acid tert-butyl ester in 1 ml of dichloromethane, 1 ml of trifluoracetic acid was added. The reaction mixture was allowed to stir at room temperature for 2-3 h while monitoring the reaction progress by LC-MS. Upon completion of the reaction, the solvent and excess of trifluoracetic acid were evaporated and the residue was dried under high vacuo for 1 hour. To the foam obtained dissolved in 1 ml of tetrahydrofurane, 0.060 g N-(3,5-difluoro-benzyl)-2-methyl-malonamic acid 0.043 g of N-(3-dimethylaminopropyl)-N'-ethylcarbodiimide hydrochloride, 0.030 g of 1-hydroxybenzotrizole hydrate and 0.087 g of N,N-diisopropyl-ethylamine were added. After stirring the mixture at room temperature for 18 h, 0.5 N HCl (1 ml) was added and the mixture was extracted with dichloromethane (2 ml) The organic layer was extracted with 0.5 N aqueous NaHCO$_3$ solution, dried (MgSO$_4$) and evaporated on the rotary evaporator. The residue was crystallized with heptane/EtOAc=4:1 to yield 0.057 g (50%) of the epimeric mixture of title compound as white solid.

MS m/e (%): 507.3 (M+H$^+$, 100).

EXAMPLE 13

N-(5-Benzenesulfonyl-1-methyl-2-oxo-2,3,4,5-tetrahydro-1H-benzo[b][1,4]diazepin-3-yl)-N'-(3,5-difluoro-benzyl)-2-methyl-malonamide a) (5-Benzenesulfonyl-1-methyl-2-oxo-2,3,4,5-tetrahydro-1H-benzo[b][1,4]diazepin-3-yl)-carbamic acid tert-butyl ester To a solution of 0.087 g (1-methyl-2-oxo-2,3,4,5-tetrahydro-1H-benzo[b][1,4]diazepin-3-yl)-carbamic acid tert-butyl ester in 1 ml of dichloromethane, 0.064 g of benzene sulfonyl chloride and 0.052 g of pyridine were added. The reaction mixture was stirred at room temperature for 16 hours. The reaction was quenched by addition of 1 M HCl (1 ml) and extracted with dichloromethane. The organic layer was washed with saturated NaHCO$_3$, dried (MgSO$_4$) and evaporated on the rotary evaporator to yield 0.113 g (95%) of the product as a light yellow foam.

MS m/e (%): 432.3 (M+H$^+$, 100).

b) N-(5-Benzenesulfonyl-1-methyl-2-oxo-2,3,4,5-tetrahydro-1H-benzo[b][1,4]diazepin-3-yl)-N'-(3,5-difluoro-benzyl)-2-methyl-malonamide The title compound was obtained in comparable yields according to the procedure described for example 12c) using (5-benzenesulfonyl-1-methyl-2-oxo-2,3,4,5-tetrahydro-1H-benzo[b][1,4]diazepin-3-yl)-carbamic acid tert-butyl ester instead of (5-benzyl-1-methyl-2-oxo-2,3,4,5-tetrahydro-1H-benzo[b][1,4]diazepin-3-yl)-carbamic acid tert-butyl ester.

MS m/e (%): 557.2 (M+H$^+$, 100).

EXAMPLE 14

N-(5-Benzoyl-1-methyl-2-oxo-2,3,4,5-tetrahydro-1H-benzo[b][1,4]diazepin-3-yl)-N'-(3,5-difluoro-benzyl)-2-methyl-malonamide a) (5-Benzoyl-1-methyl-2-oxo-2,3,4,5-tetrahydro-1H-benzo[b]1,4]diazepin-3-yl)-carbamic acid tert-butyl ester To a solution of 0.087 g (1-methyl-2-oxo-2,3,4,5-tetrahydro-1H-benzo[b][1,4]diazepin-3-yl)-carbamic acid tert-butyl ester in 1 ml of dichloromethane, 0.051 g of benzoyl chloride and 0.061 g of triethylamine were added. The reaction mixture was stirred at room temperature for 16 hours. The reaction was quenched by addition of 1 M HCl (1 ml) and extracted with dichloromethane. The organic layer was washed with saturated NaHCO$_3$, dried (MgSO$_4$) and evaporated on the rotary evaporator to yield 0.125 g (97%) of the product as a light yellow foam.

MS m/e (%): 396.3 (M+H$^+$, 100).

b) N-(5-Benzoyl-1-methyl-2-oxo-2,3,4,5-tetrahydro-1H-benzo[b][1,4]diazepin-3-yl)-N'-(3,5-difluoro-benzyl)-2-methyl-malonamide The title compound was obtained in comparable yields according to the procedure described for example 12c) using (5-benzenesulfonyl-1-methyl-2-oxo-2,3,4,5-tetrahydro-1H-benzo[b][1,4]diazepin-3-yl)-carbamic acid tert-butyl ester instead of (5-benzyl-1-methyl-2-oxo-2,3,4,5-tetrahydro-1H-benzo[b][1,4]diazepin-3-yl)-carbamic acid tert-butyl ester.

MS m/e (%): 521.3 (M+H$^+$, 100).

EXAMPLE 15

N-(7-Chloro-1-methyl-2-oxo-5-phenyl-2,3-dihydro-1H-benzo[e][1,4]diazepin-3-yl)-N'-(3,5-difluoro-benzyl)-2-methyl-malonamide The title compound was obtained in comparable yields according to the procedures described for example 1 using (3RS)-3-amino-1,3-dihydro-7-chloro-1-methyl-5-phenyl-2H-1,4-benzodiazepin-2-one instead of (3RS)-3-amino-1,3-dihydro-1-methyl-5-phenyl-2H-1,4-benzodiazepin-2-one in step d).

MS m/e (%): 525.3 (M+H$^+$, 100).

EXAMPLE 16

N-(3,5-Difluoro-benzyl)-N'-[2-(3,4-dihydro-1H-isoquinolin-2-yl)-1-(1H-indol-3-ylmethyl)-2-oxo-ethyl]-2-methyl-malonamide a) [2-(3,4-Dihydro-1H-isoquinolin-2-yl)-1-(1H-indol-3-ylmethyl)-2-oxo-ethyl]-carbamic acid tert-butyl ester tert-Butyloxycarbonyl-L-tryptophan (3.00 g, 9.9 mmol) and 1,2,3,4-tetrahydroisoquinoline (1.31 g, 9.9 mmol) were suspended in THF (20 ml). At a temperature of 0° C., hydroxybenzotriazole (1.33 g, 9.9 mmol), diisopropylethylamine (1.27 g, 9.9 mmol), and EDC (N-3-dimethylaminopropyl-N'-ethylcarbodiimide hydrochloride, 1.89 g, 9.9 mmol) were added. The reaction mixture was stirred overnight at r.t. The solvent was evaporated, the residue was taken up in ethyl acetate, washed with water, and dried (Na$_2$SO$_4$). After evaporation of the solvent, the title compound, MS: m/e=420.5 (M+H$^+$), (2.90 g, 70%) was obtained by chromatographic purification of the residue (silica gel, MeOH, CH$_2$Cl$_2$).

b) 2-Amino-1-(3,4-dihydro-1H-isoquinolin-2-yl)-3-(1H-indol-3-yl)-propan-1-one

[2-(3,4-Dihydro-1H-isoquinolin-2-yl)-1-(1H-indol-3-ylmethyl)-2-oxo-ethyl]-carbamic acid tert-butyl ester (2.90 g, 6.91 mmol) was dissolved in CH$_2$Cl$_2$ (10 ml). Trifluoroacetic acid (10 ml) was added and the mixture was stirred for 90 minutes at r.t. until analytical HPLC indicated complete consumption of the starting material. The solvent was evaporated, the residue was taken up in ethyl acetate, washed (water), and dried (Na$_2$SO$_4$). After evaporation of the solvent, the title compound, MS: m/e=320.4 (M+H$^+$), (1.73 g, 69%) was obtained by chromatographic purification of the residue (silica gel, MeOH, CH$_2$Cl$_2$).

c) N-(3,5-Difluoro-benzyl)-N'-[2-(3,4-dihydro-1H-isoquinolin-2-yl)-1-(1H-indol-3-ylmethyl)-2-oxo-ethyl]-2-methyl-malonamide 2-Amino-1-(3,4-dihydro-1H-isoquinolin-2-yl)-3-(1H-indol-3-yl)-propan-1-one (57 mg, 0.18 mmol) was placed in a disposable polypropylene tube and dissolved in DMF (1 ml). TBTU (O-(benzotriazol-1-yl)-N,N,N',N'-tetramethyluronium-tetrafluoroborate, 65 mg, 0.2 mmol) and N-(3,5-difluoro-benzyl)-2-methyl-malonamic acid (49 mg, 0.2 mmol) were added, and the mixture was shaken overnight at r.t. The title compound, MS: m/e=545.3 (M+H$^+$), was isolated from the reaction mixture by automated, preparative HPLC (YMC CombiPrep C18 column 50×20 mm, solvent gradient 5-95% CH$_3$CN in 0.1% TFA(aq) over 6.0 min, λ=230 nm, flow rate 40 ml/min).

EXAMPLE 17

N-[1-Benzyl-2-(3,4-dihydro-1H-isoquinolin-2-yl)-2-oxo-ethyl]-N'-(3,5-difluoro-benzyl)-2-methyl-malonamide The title compound, MS: m/e=506.3 (M+H$^+$), was prepared in analogy to example 16 from tert-butyloxycarbonyl-L-phenylalanine.

EXAMPLE 18

N-[1-Benzyloxymethyl-2-(3,4-dihydro-1H-isoquinolin-2-yl)-2-oxo-ethyl]-N'-(3,5-difluoro-benzyl)-2-methyl-malonamide The title compound, MS: m/e=536.4 (M+H$^+$), was prepared in analogy to example 16 from N-(tert-butoxycarbonyl)-O-benzyl-L-serine.

EXAMPLE 19

N-(3,5-Difluoro-benzyl)-N'-[2-(3,4-dihydro-1H-isoquinolin-2-yl)-2-oxo-1-(S)phenyl-ethyl]-2-methyl-malonamide The title compound, MS: m/e=492.3 (M+H$^+$), was prepared in analogy to example 16 from N-alpha-(tert-butoxycarbonyl)-L-phenylglycine.

EXAMPLE 20

N-(3,5-Difluoro-benzyl)-N'-[2-(3,4-dihydro-1H-isoquinolin-2-yl)-2-oxo-1-(R)-phenyl-ethyl]-2-methyl-malonamide The title compound, MS: m/e=492.3 (M+H$^+$), was prepared in analogy to example 16 from N-alpha-(tert-butoxycarbonyl)-D-phenylglycine.

EXAMPLE 21

N-(3,5-Difluoro-benzyl)-N'-[2-(3,4-dihydro-1H-isoquinolin-2-yl)-1-hydroxymethyl-2-oxo-ethyl]-2-methyl-malonamide The title compound, MS: m/e=446.3 (M+H$^+$), was prepared in analogy to example 16 from tert-butyloxycarbonyl-L-serine.

EXAMPLE 22

N-[1-(4-Chloro-benzyl)-2-(3,4-dihydro-1H-isoquinolin-2-yl)-2-oxo-ethyl]-N'-(3,5-difluoro-benzyl)-2-methyl-malonamide The title compound, MS: m/e=540.4 (M$^+$), was prepared in analogy to example 16 from N-alpha-(tert-butyloxycarbonyl)-p-chloro-L-phenylalanine.

EXAMPLE 23

N-[1-Benzo[b]thiophen-3-ylmethyl-2-(3,4-dihydro-1H-isoquinolin-2-yl)-2-oxo-ethyl]-N'-(3,5-difluoro-benzyl)-2-methyl-malonamide The title compound, MS: m/e=562.4 (M+H$^+$), was prepared in analogy to example 16 from N-alpha-(tert-butyloxycarbonyl)-L-benzothienylalanine.

EXAMPLE 24

N-[1-(3,4Dichloro-benzyl)-2-(3,4-dihydro-1H-isoquinolin-2-yl)-2-oxo-ethyl]-N'-(3,5-difluoro-benzyl)-2-methyl-malonamide The title compound, MS: m/e=574.3 (M$^+$), was prepared in analogy to example 16 from N-alpha-(tert-butyloxycarbonyl)-m, p-dichloro-L-phenylalanine.

EXAMPLE 25

N-[1-Cyclohexylmethyl-2-(3,4-dihydro-1H-isoquinolin-2-yl)-2-oxo-ethyl]-N'-(3,5-difluoro-benzyl)-2-methyl-malonamide The title compound, MS: m/e=511.6 (M+H$^+$), was prepared in analogy to example 16 from N-alpha-(tert-butyloxycarbonyl)-L-cyclohexylalanine.

EXAMPLE 26

N-(3,5-Difluoro-benzyl)-N'-[1-(3,4-dihydro-1H-isoquinoline-2-carbonyl)-3-methylsulfanyl-propyl]-2-methyl-malonamide The title compound, MS: m/e=490.4 (M+H$^+$), was prepared in analogy to example 16 from tert-butyloxycarbonyl-L-methionine.

EXAMPLE 27

N-(3,5-Difluoro-benzyl)-N'-[1-(3,4-dihydro-1H-isoquinoline-2-carbonyl)-pentyl]-2-methyl-malonamide The title compound, MS: m/e=472.3 (M+H$^+$), was prepared in analogy to example 16 from N-alpha-tert-butyloxycarbonyl-L-2-aminocaproic acid.

EXAMPLE 28

N-(3,5-Difluoro-benzyl)-N'-[1-(3,4-dihydro-1H-isoquinoline-2-carbonyl)-3,3-dimethyl-butyl]-2-methyl-malonamide The title compound, MS: m/e=486.4 (M+H$^+$), was prepared in analogy to example 16 from tert-butyloxycarbonyl-L-neopentylglycine.

EXAMPLE 29

N-(3,5-Difluoro-benzyl)-N'-[1-(3,4-dihydro-1H-isoquinoline-2-carbonyl)-propyl]-2-methyl-malonamide The title compound, MS: m/e=444.4 (M+H$^+$), was prepared in analogy to example 16 from tert-butyloxycarbonyl-L-2-aminobutanoic acid.

EXAMPLE 30

N-[1-(2-Cyano-benzyl)-2-(3,4-dihydro-1H-isoquinolin-2-yl)-2-oxo-ethyl]-N'-(3,5-difluoro-benzyl)-2-methyl-malonamide The title compound, MS: m/e=531.4 (M+H$^+$), was prepared in analogy to example 16 from N-alpha-(tert-butyloxycarbonyl)-o-cyano-L-phenylalanine.

EXAMPLE 31

N-(3,5-Difluoro-benzyl)-N'-[1-(3,4-dihydro-1H-isoquinoline-2-carbonyl)-2-methyl-butyl]-2-methyl-malonamide The title compound, MS: m/e=472.4 (M+H$^+$), was prepared in analogy to example 16 from tert-butyloxycarbonyl-L-isoleucine.

EXAMPLE 32

N-(3,5-Difluoro-benzyl)-N'-[1-(1H-indol-3-ylm-ethyl)-2-(6-methoxy-3,4-dihydro-1H-isoquinolin-2-yl)-2-oxo-ethyl]-2-methyl-malonamide a) 2-[2-(3,5-Difluoro-benzylcarbamoyl)-propionylamino]-3-(1H-indol-3-yl)-propionic acid tert-butyl ester N-(3,5-Difluoro-benzyl)-2-methyl-malonamic acid (3.00 g, 12.3 mmol), L-tryptophan-tert-butylester hydrochloride (3.66 g, 12.3 mmol), TBTU (O-(benzotriazol-1-yl)-N,N,N',N'-tetramethyluronium-tetrafluoroborate, 3.96 g, 12.3 mmol) and triethylamin (3.74 g, 3.70 mmol) were dissolved in DMF (15 ml) and stirred for 5 h at r.t. The reaction mixture was poured into water and the product mixture was extracted with ethyl acetate. The organic layers were dried ($Na_2SO_4$). After evaporation of the solvent, the title compound, MS: m/e=486.4 (M+H$^+$), (6.45 g, quant.) was obtained by chromatographic purification of the residue (silica gel, MeOH, $CH_2Cl_2$).

b) 2-[2-(3,5-Difluoro-benzylcarbamoyl)-propionylamino]-3-(1H-indol-3-yl)-propionic acid 2-[2-(3,5-Difluoro-benzylcarbamoyl)-propionylamino]-3-(1H-indol-3-yl)-propionic acid tert-butyl ester (5.99 g, 12.3 mmol) was dissolved in dichloromethane (15 ml), and trifluoroacetic acid (15 ml) was added at 0° C. The mixture was stirred overnight at r.t. until all starting material was consumed (analytical HPLC). The volatiles were evaporated, the residue was taken up in ethyl acetate and washed with water. The organic layers were dried ($Na_2SO_4$). After evaporation of the solvent, the title compound, MS: m/e=429.4 (M+H$^+$), (3.5 g, 66%) was obtained by chromatographic purification of the residue (silica gel, MeOH, $CH_2Cl_2$).

c) N-(3,5-Difluoro-benzyl)-N'-[1-(1H-indol-3-ylmethyl)-2-(6-methoxy-3,4-dihydro-1H-isoquinolin-2-yl)-2-oxo-ethyl]-2-methyl-malonamide 2-[2-(3,5-Difluoro-benzylcarbamoyl)-propionylamino]-3-(1H-indol-3-yl)-propionic acid (64 mg, 0.15 mmol) was placed in a disposable polypropylene tube and dissolved in DMF (1 ml). TPTU (O-[2-oxo-1(2H)-pyridyl]-N,N,N',N'-tetramethyluronium-tetrafluoroborate, 49 mg, 0.165 mmol) and 6-methoxy-1,2,3,4-tetrahydro-isoquinoline (24 mg, 0.15 mmol) were added, and the mixture was shaken overnight at r.t. The title compound, MS: m/e=575.3 (M+H$^+$), was isolated from the reaction mixture by automated, preparative HPLC (YMC CombiPrep C18 column 50×20 mm, solvent gradient 5-95% $CH_3CN$ in 0.1% TFA(aq) over 6.0 min, λ=230 nm, flow rate 40 ml/min).

EXAMPLE 33

N-{1-Benzyl-2-[1-(2,5-dimethyl-2H-pyrazol-3-yl)-3,4-dihydro-1H-isoquinolin-2-yl]-2-oxo-ethyl}-N'-(3,5-difluoro-benzyl)-2-methyl-malonamide The title compound, MS: m/e=600.3 (M+H$^+$), was prepared in analogy to example 32 from L-phenylalanine-tert-butylester hydrochloride and (RS)-1-(2,5-Dimethyl-2H-pyrazol-3-yl)-1,2,3,4-tetrahydro-isoquinoline.

EXAMPLE 34

N-[1-Benzyl-2-(5-benzyloxy-3,4-dihydro-1H-isoquinolin-2-yl)-2-oxo-ethyl]-N'-(3,5-difluoro-benzyl)-2-methyl-malonamide The title compound, MS: m/e=612.3 (M+H$^+$), was prepared in analogy to example 32 from L-phenylalanine-tert-butylester hydrochloride and 5-benzyloxy-1,2,3,4-tetrahydro-isoquinoline.

EXAMPLE 35

N-[2-(8-Chloro-3,4-dihydro-1H-isoquinolin-2-yl)-1-(1H-indol-3-ylmethyl)-2-oxo-ethyl]-N'-(3,5-difluoro-benzyl)-2-methyl-malonamide The title compound, MS: m/e=579.3 (M+H$^+$), was prepared in analogy to example 32 from 8-chloro-1,2,3,4-tetrahydro-isoquinoline.

EXAMPLE 36

N-[1-Benzyl-2-(6-methoxy-3,4-dihydro-1H-isoquinolin-2-yl)-2-oxo-ethyl]-N'-(3,5-difluoro-benzyl)-2-methyl-malonamide The title compound, MS: m/e=536.4 (M+H$^+$), was prepared in analogy to example 32 from L-phenylalanine-tert-butylester hydrochloride and 6-methoxy-1,2,3,4-tetrahydro-isoquinoline.

EXAMPLE 37

N-(3,5-Difluoro-benzyl)-N'-[2-(7,8-dimethoxy-3,4-dihydro-1H-isoquinolin-2-yl)-1-(1H-indol-3-ylm-ethyl)-2-oxo-ethyl]-2-methyl-malonamide The title compound, MS: m/e=605.3 (M+H$^+$), was prepared in analogy to example 32 from 7,8-dimethoxy-1,2,3,4-tetrahydro-isoquinoline.

EXAMPLE 38

N-[1-Benzyl-2-oxo-2-(1-pyrazin-2-yl-3,4-dihydro-1H-isoquinolin-2-yl)-ethyl]-N'-(3,5-difluoro-benzyl)-2-methyl-malonamide The title compound, MS: m/e=584.4 (M+H$^+$), was prepared in analogy to example 32 from L-phenylalanine-tert-butylester hydrochloride and (RS)-1-pyrazin-2-yl-1,2,3,4-tetrahydro-isoquinoline.

EXAMPLE 39

N-[1-Benzyl-2-(4-methyl-3,4-dihydro-1H-isoquinolin-2-yl)-2-oxo-ethyl]-N'-(3,5-difluoro-benzyl)-2-methyl-malonamide The title compound, MS: m/e=520.3 (M+H$^+$), was prepared in analogy to example 32 from L-phenylalanine-tert-butylester hydrochloride and 4-methyl-1,2,3,4-tetrahydro-isoquinoline.

EXAMPLE 40

N-(3,5-Difluoro-benzyl)-N'-[2-(1,3-dihydro-isoindol-2-yl)-1-(1H-indol-3-ylmethyl)-2-oxo-ethyl]-2-methyl-malonamide The title compound, MS: m/e=531.3 (M+H$^+$), was prepared in analogy to example 32 from isoindoline.

EXAMPLE 41

N-(3,5-Difluoro-benzyl)-N'-[2-(6,9-dihydro-7H-[1,3]dioxolo[4,5-h]isoquinolin-8-yl)-1-(1H-indol-3-ylmethyl)-2-oxo-ethyl]-2-methyl-malonamide The title compound, MS: m/e=589.5 (M+H$^+$), was prepared in analogy to example 32 from 6,7,8,9-tetrahydro-[1,3]dioxolo[4,5-h]isoquinoline.

EXAMPLE 42

N-[1-Benzyl-2-oxo-2-(1-pyridin-2-yl-3,4-dihydro-1H-isoquinolin-2-yl)-ethyl]-N'-(3,5-difluoro-benzyl)-2-methyl-malonamide The title compound, MS: m/e=583.4 (M+H$^+$), was prepared in analogy to example 32 from L-phenylalanine-tert-butylester hydrochloride and 1,2,3,4-tetrahydro-1-(2-pyridyl)isoquinoline.

EXAMPLE 43

N-(3,5-Difluoro-benzyl)-N'-[1-(1H-indol-3-ylmethyl)-2-(4-methyl-3,4-dihydro-1H-isoquinolin-2-yl)-2-oxo-ethyl]-2-methyl-malonamide The title compound, MS: m/e=559.4 (M+H$^+$), was prepared in analogy to example 32 from 4-methyl-1,2,3,4-tetrahydro-isoquinoline.

EXAMPLE 44

N-[2-(9-Aza-tricyclo[6.2.2.0 2,7]dodeca-2,4,6-trien-9-yl)-1-benzyl-2-oxo-ethyl]-N'-(3,5-difluoro-benzyl)-2-methyl-malonamide The title compound, MS: m/e=532.4 (M+H$^+$), was prepared in analogy to example 32 from L-phenylalanine-tert-butylester hydrochloride and 9-aza-tricyclo[6.2.2.0 2,7]dodeca-2,4,6-triene.

EXAMPLE 45

N-(3,5-Difluoro-benzyl)-N'-[1-(1H-indol-3-ylmethyl)-2-oxo-2-(6,7,8-trimethoxy-3,4-dihydro-1H-isoquinolin-2-yl)-ethyl]-2-methyl-malonamide The title compound, MS: m/e=635.4 (M+H$^+$), was prepared in analogy to example 32 from 6,7,8-trimethoxy-1,2,3,4-tetrahydro-isoquinoline.

EXAMPLE 46

N-{1-Benzyl-2-[7-(4-methyl-piperazine-1-sulfonyl)-3,4-dihydro-1H-isoquinolin-2-yl]-2-oxo-ethyl}-N'-(3,5-difluoro-benzyl)-2-methyl-malonamide The title compound, MS: m/e=668.5 (M+H$^+$), was prepared in analogy to example 32 from L-phenylalanine-tert-butylester hydrochloride and 7-(4-methyl-piperazine-1-sulfonyl)-1,2,3,4-tetrahydro-isoquinoline.

EXAMPLE 47

N-[1-Benzyl-2-oxo-2-(1,3,4,9-tetrahydro-b-carbolin-2-yl)-ethyl]-N'-(3,5-difluoro-benzyl)-2-methyl-malonamide The title compound, MS: m/e=545.3 (M+H$^+$), was prepared in analogy to example 32 from L-phenylalanine-tert-butylester hydrochloride and 1,2,3,4-tetrahydro-beta-carboline.

EXAMPLE 48

N-[1-Benzyl-2-(5-chloro-3,4-dihydro-1H-isoquinolin-2-yl)-2-oxo-ethyl]-N'-(3,5-difluoro-benzyl)-2-methyl-malonamide The title compound, MS: m/e=540.4 (M$^+$), was prepared in analogy to example 32 from L-phenylalanine-tert-butylester hydrochloride and 5-chloro-1,2,3,4-tetrahydro-isoquinoline.

EXAMPLE 49

N-(3,5-Difluoro-benzyl)-N'-[2-(4,4-difluoro-piperidin-1-yl)-1-(1H-indol-3-ylmethyl)-2-oxo-ethyl]-2-methyl-malonamide The title compound, MS: m/e=533.4 (M+H$^+$), was prepared in analogy to example 32 from 4,4-difluoropiperidine.

EXAMPLE 50

N-[1-Benzyl-2-(7,8-dihydro-5H-[1,3]dioxolo[4,5-g]isoquinolin-6-yl)-2-oxo-ethyl]-N'-(3,5-difluoro-benzyl)-2-methyl-malonamide The title compound, MS: m/e=550.3 (M+H$^+$), was prepared in analogy to example 32 from L-phenylalanine-tert-butylester hydrochloride and 5,6,7,8-tetrahydro-1,3-dioxolo(4,5-G)isoquinoline.

EXAMPLE 51

N-[1-Benzyl-2-oxo-2-(1-pyrimidin-5-yl-3,4-dihydro-1H-isoquinolin-2-yl)-ethyl]-N'-(3,5-difluoro-benzyl)-2-methyl-malonamide The title compound, MS: m/e=584.4 (M+H$^+$), was prepared in analogy to example 32 from L-phenylalanine-tert-butylester hydrochloride and 1-pyrimidin-5-yl-1,2,3,4-tetrahydro-isoquinoline.

EXAMPLE 52

N-(3,5-Difluoro-benzyl)-N'-[1-(1H-indol-3-ylm-ethyl)-2-(3-methyl-piperidin-1-yl)-2-oxo-ethyl]-2-methyl-malonamide The title compound, MS: m/e=511.4 (M+H$^+$), was prepared in analogy to example 32 from 3-methylpiperidine.

EXAMPLE 53

N-[1-Benzyl-2-(6,7-dimethoxy-3,4-dihydro-1H-iso-quinolin-2-yl)-2-oxo-ethyl]-N'-(3,5-difluoro-benzyl)-2-methyl-malonamide The title compound, MS: m/e=566.3 (M+H$^+$), was prepared in analogy to example 32 from L-phenylalanine-tert-butylester hydrochloride and 6,7-dimethoxy-1,2,3,4-tetrahydro-isoquinoline.

EXAMPLE 54

N-[1-Benzyl-2-(octahydro-isoquinolin-2-yl)-2-oxo-ethyl]-N'-(3,5-difluoro-benzyl)-2-methyl-malona-mide The title compound, MS: m/e=512.3 (M+H$^+$), was prepared in analogy to example 32 from L-phenylalanine-tert-butylester hydrochloride and trans-decahydroisoquinoline.

EXAMPLE 55

N-[1-Benzyl-2-(1,3-dihydro-isoindol-2-yl)-2-oxo-ethyl]-N'-(3,5-difluoro-benzyl)-2-methyl-malona-mide The title compound, MS: m/e=492.4 (M+H$^+$), was prepared in analogy to example 32 from L-phenylalanine-tert-butylester hydrochloride and Isoindoline.

EXAMPLE 56

N-(3,5-Difluoro-benzyl)-N'-[2-(3,6-dihydro-2H-pyridin-1-yl)-1-(1H-indol-3-ylmethyl)-2-oxo-ethyl]-2-methyl-malonamide The title compound, MS: m/e=494.6 (M+H$^+$), was prepared in analogy to example 32 from 1,2,3,6-tetrahydropyridine.

EXAMPLE 57

N-[1-Benzyl-2-(6,9-dihydro-7H-[1,3]dioxolo[4,5-h]isoquinolin-8-yl)-2-oxo-ethyl]-N'-(3,5-difluoro-benzyl)-2-methyl-malonamide The title compound, MS: m/e=550.3 (M+H$^+$), was prepared in analogy to example 32 from L-phenylalanine-tert-butylester hydrochloride and 6,7,8,9-tetrahydro-[1,3]dioxolo[4,5-h]isoquinoline.

EXAMPLE 58

N-[1-Benzyl-2-oxo-2-(6,7,8-trimethoxy-3,4-dihydro-1H-isoquinolin-2-yl)-ethyl]-N'-(3,5-difluoro-benzyl)-2-methyl-malonamide The title compound, MS: m/e=596.3 (M+H$^+$), was prepared in analogy to example 32 from L-phenylalanine-tert-butylester hydrochloride and 6,7,8-trimethoxy-1,2,3,4-tetrahydro-isoquinoline.

EXAMPLE 59

N-(1-Benzyl-2-oxo-2-piperidin-1-yl-ethyl)-N'-(3,5-difluoro-benzyl)-2-methyl-malonamide The title compound, MS: m/e=458.3 (M+H$^+$), was prepared in analogy to example 32 from L-phenylalanine-tert-butylester hydrochloride and piperidine.

EXAMPLE 60

N-(3,5-Difluoro-benzyl)-N'-[2-(4-fluoro-piperidin-1-yl)-1-(1H-indol-3-ylmethyl)-2-oxo-ethyl]-2-methyl-malonamide The title compound, MS: m/e=515.4 (M+H$^+$), was prepared in analogy to example 32 from 4-fluoropiperidine.

EXAMPLE 61

N-(3,5-Difluoro-benzyl)-N'-[2-(6,7-dimethoxy-3,4-dihydro-1H-isoquinolin-2-yl)-1-(1H-indol-3-ylm-ethyl)-2-oxo-ethyl]-2-methyl-malonamide The title compound, MS: m/e=605.3 (M+H$^+$), was prepared in analogy to example 32 from 6,7-dimethoxy-1,2,3,4-tetrahydro-isoquinoline.

EXAMPLE 62

N-(3,5-Difluoro-benzyl)-N'-[2-(2,5-dihydro-pyrrol-1-yl)-1-(1H-indol-3-ylmethyl)-2-oxo-ethyl]-2-methyl-malonamide The title compound, MS: m/e=481.4(M+H$^+$), was prepared in analogy to example 32 from 1-isopropyl-1,2,3,4-tetrahydro-isoquinoline.

EXAMPLE 63

N-[1-Benzyl-2-(1-isopropyl-3,4-dihydro-1H-iso-quinolin-2-yl)-2-oxo-ethyl]-N'-(3,5-difluoro-benzyl)-2-methyl-malonamide The title compound, MS: m/e=548.4 (M+H$^+$), was prepared in analogy to example 32 from L-phenylalanine-tert-butylester hydrochloride and isopropyl-1,2,3,4-tetrahydro-isoquinoline.

EXAMPLE 64

N-[1-Benzyl-2-(3,6-dihydro-2H-pyridin-1-yl)-2-oxo-ethyl]-N'-(3,5-difluoro-benzyl)-2-methyl-malonamide The title compound, MS: m/e=456.4 (M+H$^+$), was prepared in analogy to example 32 from L-phenylalanine-tert-butylester hydrochloride and 8-chloro-1,2,3,4-tetrahydro-isoquinoline.

EXAMPLE 65

N-[1-Benzyl-2-(8-chloro-3,4-dihydro-1H-isoquinolin-2-yl)-2-oxo-ethyl]-N'-(3,5-difluoro-benzyl)-2-methyl-malonamide The title compound, MS: m/e=540.4 (M+H$^+$), was prepared in analogy to example 32 from L-phenylalanine-tert-butylester hydrochloride and 8-chloro-1,2,3,4-tetrahydro-isoquinoline.

EXAMPLE 66

N-[1-Benzyl-2-(1-cyanomethyl-6,7-dimethoxy-3,4-dihydro-1H-isoquinolin-2-yl)-2-oxo-ethyl]-N'-(3,5-difluoro-benzyl)-2-methyl-malonamide The title compound, MS: m/e=605.4 (M+H$^+$), was prepared in analogy to example 32 from L-phenylalanine-tert-butylester hydrochloride and 1-cyanomethyl-6,7-dimethoxy-1,2,3,4-tetrahydro-isoquinoline.

EXAMPLE 67

N-[1-Benzyl-2-(7-bromo-3,4-dihydro-1H-isoquinolin-2-yl)-2-oxo-ethyl]-N'-(3,5-difluoro-benzyl)-2-methyl-malonamide The title compound, MS: m/e=586.3 (M+H$^+$), was prepared in analogy to example 32 from L-phenylalanine-tert-butylester hydrochloride and 7-bromo-1,2,3,4-tetrahydro-isoquinoline.

EXAMPLE 68

N-[2-(6,7-Diethoxy-3,4-dihydro-1H-isoquinolin-2-yl)-1-(1H-indol-3-ylmethyl)-2-oxo-ethyl]-N'-(3,5-difluoro-benzyl)-2-methyl-malonamide The title compound, MS: m/e=633.4 (M+H$^+$), was prepared in analogy to example 32 from 6,7-diethoxy-1,2,3,4-tetrahydro-isoquinoline.

EXAMPLE 69

N-[2-(4-Amino-1,3-dihydro-isoindol-2-yl)-1-(1H-indol-3-ylmethyl)-2-oxo-ethyl]-N'-(3,5-difluoro-benzyl)-2-methyl-malonamide The title compound, MS: m/e=546.4 (M+H$^+$), was prepared in analogy to example 32 from 2,3-dihydro-1H-isoindol-4-ylamine.

EXAMPLE 70

N-[2-(5-Chloro-3,4-dihydro-1H-isoquinolin-2-yl)-1-(1H-indol-3-ylmethyl)-2-oxo-ethyl]-N'-(3,5-difluoro-benzyl)-2-methyl-malonamide The title compound, MS: m/e=579.3 (M$^+$), was prepared in analogy to example 32 from 8-chloro-1,2,3,4-tetrahydro-isoquinoline.

EXAMPLE 71

N-(3,5-Difluoro-benzyl)-N'-[1-(1H-indol-3-ylmethyl)-2-oxo-2-pyrrolidin-1-yl-ethyl]-2-methyl-malonamide The title compound, MS: m/e=483.3 (M+H$^+$), was prepared in analogy to example 32 from pyrrolidine.

EXAMPLE 72

N-(3,5-Difluoro-benzyl)-N'-[1-(1H-indol-3-ylmethyl)-2-(2-methoxymethyl-pyrrolidin-1-yl)-2-oxo-ethyl]-2-methyl-malonamide The title compound, MS: m/e=527.3 (M+H$^+$), was prepared in analogy to example 32 from 2-methoxymethyl-pyrrolidin.

EXAMPLE 73

N-[2-(7,8-Dichloro-3,4-dihydro-1H-isoquinolin-2-yl)-1-(1H-indol-3-ylmethyl)-2-oxo-ethyl]-N'-(3,5-difluoro-benzyl)-2-methyl-malonamide The title compound, MS: m/e=613.3 (M+H$^+$), was prepared in analogy to example 32 from 7,8-dichloro-1,2,3,4-tetrahydro-isoquinoline.

EXAMPLE 74

N-[1-(Benzyl-methyl-carbamoyl)-2-phenyl-ethyl]-N'-(3,5-difluoro-benzyl)-2-methyl-malonamide The title compound, MS: m/e=494.4 (M+H$^+$), was prepared in analogy to example 32 from L-phenylalanine-tert-butylester hydrochloride and benzyl-methyl-amine.

EXAMPLE 75

N-[2-Azepan-1-yl-1-(1H-indol-3-ylmethyl)-2-oxo-ethyl]-N'-(3,5-difluoro-benzyl)-2-methyl-malonamide The title compound, MS: m/e=511.4 (M+H$^+$), was prepared in analogy to example 32 from azepane.

EXAMPLE 76

N-(3,5-Difluoro-benzyl)-N'-[1-dimethylcarbamoyl-2-(1H-indol-3-yl)-ethyl]-2-methyl-malonamide The title compound, MS: m/e=457.5 (M+H$^+$), was prepared in analogy to example 32 from dimethylamine.

EXAMPLE 77

N-(3,5-Difluoro-benzyl)-N'-[1-(1H-indol-3-ylmethyl)-2-(7-nitro-3,4-dihydro-1H-isoquinolin-2-yl)-2-oxo-ethyl]-2-methyl-malonamide The title compound, MS: m/e=590.4 (M+H$^+$), was prepared in analogy to example 32 from 7-nitro-1,2,3,4-tetrahydro-isoquinoline.

EXAMPLE 78

N-[1-Benzyl-2-(1-cyclopropyl-6,7-dimethoxy-3,4-dihydro-1H-isoquinolin-2-yl)-2-oxo-ethyl]-N'-(3,5-difluoro-benzyl)-2-methyl-malonamide The tide compound, MS: m/e=606.5 (M+H$^+$), was prepared in analogy to example 32 from L-phenylalanine-tert-butylester hydrochloride and 1-cyclopropyl-6,7-dimethoxy-1,2,3,4-tetrahydro-isoquinoline.

EXAMPLE 79

N-[2-(7-Chloro-3,4-dihydro-1H-isoquinolin-2-yl)-1-(1H-indol-3-ylmethyl)-2-oxo-ethyl]-N'-(3,5-difluoro-benzyl)-2-methyl-malonamide The title compound, MS: m/e=579.3 (M+H$^+$), was prepared in analogy to example 32 from 7-chloro-1,2,3,4-tetrahydro-isoquinoline.

EXAMPLE 80

N-(1-Benzyl-2-oxo-2-pyrrolidin-1-yl-ethyl)-N'-(3,5-difluoro-benzyl)-2-methyl-malonamide The title compound, MS: m/e=444.4 (M+H$^+$), was prepared in analogy to example 32 from L-phenylalanine-tert-butylester hydrochloride and pyrrolidine.

EXAMPLE 81

N-[1-Benzyl-2-(7,8-dimethoxy-3,4-dihydro-1H-isoquinolin-2-yl)-2-oxo-ethyl]-N'-(3,5-difluoro-benzyl)-2-methyl-malonamide The title compound, MS: m/e=566.4 (M+H$^+$), was prepared in analogy to example 32 from L-phenylalanine-tert-butylester hydrochloride and 7,8-dimethoxy-1,2,3,4-tetrahydro-isoquinoline.

EXAMPLE 82

N-(3,5-Difluoro-benzyl)-N'-[1-(furan-2-ylmethyl-methyl-carbamoyl)-2-(1H-indol-3-yl)-ethyl]-2-methyl-malonamide The title compound, MS: m/e=523.3 (M+H$^+$), was prepared in analogy to example 32 from furan-2-ylmethyl-methyl-amine.

EXAMPLE 83

N-[2-(7-Bromo-3,4-dihydro-1H-isoquinolin-2-yl)-1-(1H-indol-3-ylmethyl)-2-oxo-ethyl]-N'-(3,5-difluoro-benzyl)-2-methyl-malonamide The title compound, MS: m/e=625.3 (M+H$^+$), was prepared in analogy to example 32 from 7-bromo-1,2,3,4-tetrahydro-isoquinoline.

EXAMPLE 84

N-(3,5-Difluoro-benzyl)-N'-[1-(1H-indol-3-ylmethyl)-2-(1-methyl-3,4-dihydro-1H-isoquinolin-2-yl)-2-oxo-ethyl]-2-methyl-malonamide The title compound, MS: m/e=559.4 (M+H$^+$), was prepared in analogy to example 32 from 1-methyl-1,2,3,4-tetrahydro-isoquinoline.

EXAMPLE 85

N-(3,5-Difluoro-benzyl)-N'-[2-(1-hydroxy-2,2a,4,5-tetrahydro-1H-3-aza-acenaphthylen-3-yl)-1-(1H-indol-3-ylmethyl)-2-oxo-ethyl]-2-methyl-malonamide The title compound, MS: m/e=587.4 (M+H$^+$), was prepared in analogy to example 32 from 1,2,2a,3,4,5-hexahydro-3-aza-acenaphthylen-1-ol.

EXAMPLE 86

N-(3,5-Difluoro-benzyl)-2-methyl-N'-[1-(methyl-prop-2-ynyl-carbamoyl)-2-phenyl-ethyl]-malonamide The title compound, MS: m/e=442.3 (M+H$^+$), was prepared in analogy to example 32 from L-phenylalanine-tert-butylester hydrochloride and methylpropargylamine.

EXAMPLE 87

N-(3,5-Difluoro-benzyl)-N'-[1-(1H-indol-3-ylmethyl)-2-(2-methoxymethyl-pyrrolidin-1-yl)-2-oxo-ethyl]-2-methyl-malonamide The title compound, MS: m/e=527.4 (M+H$^+$), was prepared in analogy to example 32 from 2-methoxymethyl-pyrrolidin.

EXAMPLE 80

N-(3,5-Difluoro-benzyl)-N'-[1-(1H-indol-3-ylmethyl)-2-oxo-2-piperidin-1-yl-ethyl]-2-methyl-malonamide The title compound, MS: m/e=497.4 (M+H$^+$), was prepared in analogy to example 32 from piperidine.

EXAMPLE 89

N-[1-Benzyl-2-(6-methoxy-1,3,4,9-tetrahydro-b-carbolin-2-yl)-2-oxo-ethyl]-N'-(3,5-difluoro-benzyl)-2-methyl-malonamide The title compound, MS: m/e=575.5 (M+H$^+$), was prepared in analogy to example 32 from L-phenylalanine-tert-butylester hydrochloride and 8-methoxy-2,3,4,5-tetrahydro-1H-pyrido[4,3-b]indole.

EXAMPLE 90

N-(3,5-Difluoro-benzyl)-N'-[2-(4-hydroxy-3,4-dihydro-1H-isoquinolin-2-yl)-1-(1H-indol-3-ylmethyl)-2-oxo-ethyl]-2-methyl-malonamide The title compound, MS: m/e=561.5 (M+H$^+$), was prepared in analogy to example 32 from 4-hydroxy-1,2,3,4-tetrahydro-isoquinoline.

EXAMPLE 91

N-[1-Benzyl-2-(6-fluoro-1,3,4,5-tetrahydro-pyrido[4,3-b]indol-2-yl)-2-oxo-ethyl]-N'-(3,5-difluoro-benzyl)-2-methyl-malonamide The title compound, MS: m/e=563.4 (M+H$^+$), was prepared in analogy to example 32 from L-phenylalanine-tert-butylester hydrochloride and 6-fluoro-2,3,4,5-tetrahydro-1H-pyrido[4,3-b]indole.

EXAMPLE 92

N-(3,5-Difluoro-benzyl)-N'-[1-(ethyl-methyl-carbamoyl)-2-(1H-indol-3-yl)-ethyl]-2-methyl-malonamide The title compound, MS: m/e=471.3 (M+H$^+$), was prepared in analogy to example 32 from ethylmethylamine.

EXAMPLE 93

N-(3,5-Difluoro-benzyl)-N'-[1-(1H-indol-3-ylmethyl)-2-(2-methyl-piperidin-1-yl)-2-oxo-ethyl]-2-methyl-malonamide The title compound, MS: m/e=511.5 (M+H$^+$), was prepared in analogy to example 32 from 2-methylpiperidine.

EXAMPLE 94

N-(3,5-Difluoro-benzyl)-N'-(1-{[2-(3,4-dimethoxy-phenyl)-ethyl]-methyl-carbamoyl}-2-phenyl-ethyl)-2-methyl-malonamide The title compound, MS: m/e=568.4 (M+H$^+$), was prepared in analogy to example 32 from L-phenylalanine-tert-butylester hydrochloride and N-methylhomoveratrylamine.

EXAMPLE 95

N-[2-Azetidin-1-yl-1-(1H-indol-3-ylmethyl)-2-oxo-ethyl]-N'-(3,5-difluoro-benzyl)-2-methyl-malonamide The title compound, MS: m/e=469.3 (M+H$^+$), was prepared in analogy to example 32 from azetidine.

EXAMPLE 96

N-(3,5-Difluoro-benzyl)-N'-[1-([1,3]dioxolan-2-ylmethyl-methyl-carbamoyl)-2-(1H-indol-3-yl)-ethyl]-2-methyl-malonamide The title compound, MS: m/e=529.4 (M+H$^+$), was prepared in analogy to example 32 from 2-methylaminomethyl-1,3-dioxolane.

EXAMPLE 97

N-(3,5-Difluoro-benzyl)-N'-[2-(4-hydroxymethyl-piperidin-1-yl)-1-(1H-indol-3-ylmethyl)-2-oxo-ethyl]-2-methyl-malonamide The title compound, MS: m/e=527.3 (M+H$^+$), was prepared in analogy to example 32 from 4-hydroxymethylpiperidine.

EXAMPLE 98

N-[1-Benzyl-2-(8-fluoro-1,3,4,5-tetrahydro-pyrido[4,3-b]indol-2-yl)-2-oxo-ethyl]-N'-(3,5-difluoro-benzyl)-2-methyl-malonamide The title compound, MS: m/e=563.4 (M+H$^+$), was prepared in analogy to example 32 from L-phenylalanine-tert-butylester hydrochloride and 8-fluoro-2,3,4,5-tetrahydro-1H-pyrido[4,3-b]indole.

EXAMPLE 99

N-(3,5-Difluoro-benzyl)-N'-[2-(3,4-dihydro-1H-isoquinolin-2-yl)-1-(1H-indol-3-ylmethyl)-2-oxo-ethyl]-2-propyl-malonamide a) N-(3,5-difluoro-benzyl)-2-propyl-malonamic acid was prepared in analogy to N-(3,5-difluoro-benzyl)-2-methyl-malonamic acid (example 1) from diethyl propyl-malonate.

b) N-(3,5-Difluoro-benzyl)-N'-[2-(3,4-dihydro-1H-isoquinolin-2-yl)-1-(1H-indol-3-ylmethyl)-2-oxo-ethyl]-2-propyl-malonamide. MS: m/e=573.4 (M+H$^+$), was prepared in analogy to N-(3,5-difluoro-benzyl)-N'-[2-(3,4-dihydro-1H-isoquinolin-2-yl)-1-(1H-indol-3-ylmethyl)-2-oxo-ethyl]-2-methyl-malonamide (example 16) from N-(3,5-difluoro-benzyl)-2-propyl-malonamic acid.

EXAMPLE 100

N-(3,5-Difluoro-benzyl)-N'-[2-(3,4-dihydro-1H-isoquinolin-2-yl)-1-(1H-indol-3-ylmethyl)-2-oxo-ethyl]-2-isopropyl-malonamide a) N-(3,5-Difluoro-benzyl)-2-isopropyl-malonamic acid was prepared in analogy to N-(3,5-difluoro-benzyl)-2-methyl-malonamic acid (example 1) from diethyl isopropyl-malonate.

b) N-(3,5-Difluoro-benzyl)-N'-[2-(3,4-dihydro-1H-isoguinolin-2-yl)-1-(1H-indol-3-ylmethyl)-2-oxo-ethyl]-2-isopropyl-malonamide. MS: m/e=573.3 (M+H$^+$), was prepared in analogy to N-(3,5-difluoro-benzyl)-N'-[2-(3,4-dihydro-1H-isoquinolin-2-yl)-1-(1H-indol-3-ylmethyl)-2-oxoethyl]-2-methyl-malonamide (example 16) from N-(3,5-difluoro-benzyl)-2-isopropyl-malonamic acid.

EXAMPLE 101

N-(3,5-Difluoro-benzyl)-N'-[2-(3,4-dihydro-1H-isoquinolin-2-yl)-1-(1H-indol-3-ylmethyl)-2-oxo-ethyl]-2-ethyl-malonamide a) N-(3,5-Difluoro-benzyl)-2-ethyl-malonamic acid was prepared in analogy to N-(3,5-difluoro-benzyl)-2-methyl-malonamic acid (example 1) from diethyl ethyl-malonate.
b) N-(3,5-Difluoro-benzyl)-N'-[2-(3,4-dihydro-1H-isoquinolin-2-yl)-1-(1H-indol-3-ylmethyl)-2-oxo-ethyl]-2-ethyl-malonamide, MS: m/e=559.4 (M+H$^+$), was prepared in analogy to N-(3,5-difluoro-benzyl)-N'-[2-(3,4-dihydro-1H-isoquinolin-2-yl)-1-(1H-indol-3-ylmethyl)-2-oxo-ethyl]-2-methyl-malonamide (example 16) from N-(3,5-difluoro-benzyl)-2-ethyl-malonamic acid.

EXAMPLE 102

2-Allyl-N-(3,5-difluoro-benzyl)-N'-[2-(3,4-dihydro-1H-isoquinolin-2-yl)-1-(1H-indol-3-ylmethyl)-2-oxo-ethyl]-malonamide a) N-(3,5-Difluoro-benzyl)-2-allyl-malonamic acid was prepared in analogy to N-(3,5-difluoro-benzyl)-2-methyl-malonamic acid (example 1) from diethyl allyl-malonate.
b) N-(3,5-Difluoro-benzyl)-N'-[2-(3,4-dihydro-1H-isoquinolin-2-yl)-1-(1H-indol-3-ylmethyl)-2-oxo-ethyl]-2-allyl-malonamide. MS: m/e=571.4 (M+H$^+$), was prepared in analogy to N-(3,5-difluoro-benzyl)-N'-[2-(3,4-dihydro-1H-isoquinolin-2-yl)-1-(1H-indol-3-ylmethyl)-2-oxo-ethyl]-2-methyl-malonamide (example 16) from N-(3,5-difluoro-benzyl)-2-allyl-malonamic acid.

EXAMPLE 103

N-(3,5-Difluoro-benzyl)-N'-[2-(3,4-dihydro-1H-isoquinolin-2-yl)-1-(1H-indol-3-ylmethyl)-2-oxo-ethyl]-2-fluoro-2-methyl-malonamide a) N-(3,5-Difluoro-benzyl)-2-fluoro-2-methyl-malonamic acid was prepared in analogy to N-(3,5-difluoro-benzyl)-2-methyl-malonamic acid (example 1) from diethyl 2-fluoro-2-methyl-malonate.
b) N-(3,5-Difluoro-benzyl)-N'-[2-(3,4-dihydro-1H-isoquinolin-2-yl)-1-(1H-indol-3-ylmethyl)-2-oxo-ethyl]-2-fluoro-2-methyl-malonamide, MS: m/e=563.4 (M+H$^+$), was prepared in analogy to N-(3,5-difluoro-benzyl)-N'-[2-(3,4-dihydro-1H-isoquinolin-2-yl)-1-(1H-indol-3-ylmethyl)-2-oxo-ethyl]-2-methyl-malonamide (example 16) from N-(3,5-difluoro-benzyl)-2-fluoro-2-methyl-malonamic acid.

EXAMPLE 104

N-(3,5-Difluoro-benzyl)-N'-[2-(3,4-dihydro-1H-isoquinolin-2-yl)-1-(1H-indol-3-ylmethyl)-2-oxo-ethyl]-malonamide a) N-(3,5-Difluoro-benzyl)-malonamic acid was prepared in analogy to N-(3,5-difluoro-benzyl)-2-methyl-malonamic acid (example 1) from diethyl malonate.
b) N-(3,5-Difluoro-benzyl)-N'-[2-(3,4-dihydro-1H-isoquinolin-2-yl)-1-(1H-indol-3-ylmethyl)-2-oxo-ethyl]-malonamide, MS: m/e=531.3 (M+H$^+$), was prepared in analogy to N-(3,5-difluoro-benzyl)-N'-[2-(3,4-dihydro-1H-isoquinolin-2-yl)-1-(1H-indol-3-ylmethyl)-2-oxo-ethyl]-2-methyl-malonamide (example 16) from N-(3,5-difluoro-benzyl)-malonamic acid.

EXAMPLE 105

N-(3,5-Difluoro-benzyl)-N'-[2-(3,4-dihydro-1H-isoquinolin-2-yl)-1-(1H-indol-3-ylmethyl)-2-oxo-ethyl]-2,2-dimethyl-malonamide a) N-(3,5-Difluoro-benzyl)-2,2-dimethyl-malonamic acid was prepared in analogy to N-(3,5-difluoro-benzyl)-2-methyl-malonamic acid (example 1) from diethyl 2,2-dimethyl-malonate.
b) N-(3,5-Difluoro-benzyl)-N'-[2-(3,4-dihydro-1H-isoquinolin-2-yl)-1-(1H-indol-3-ylmethyl)-2-oxo-ethyl]-2,2-dimethyl-malonamide. MS: m/e=559.3 (M+H$^+$), was prepared in analogy to N-(3,5-difluoro-benzyl)-N'-[2-(3,4-dihydro-1H-isoquinolin-2-yl)-1-(1H-indol-3-ylmethyl)-2-oxo-ethyl]-2-methyl-malonamide (example 16) from N-(3,5-difluoro-benzyl)-2,2-dimethyl-malonamic acid.

EXAMPLE 106

N-(7-Chloro-1-methyl-2-oxo-5-phenyl-2,3-dihydro-1H-benzo[e][1,4]diazepin-3-yl)-N'-(3,5-difluoro-benzyl)-2-methyl-malonamide The title compound, MS: m/e=525.1 (M+H$^+$), was prepared in analogy to example 16 from 3-amino-7-chloro-1,3-dihydro-1-methyl-5-phenyl-2H-1,4-benzodiazepin-2-one.

EXAMPLE 107

N-(3,5-Difluoro-benzyl)-N'-(1-methyl-2-oxo-5-phenyl-2,3-dihydro-1H-benzo[e][1,4]diazepin-3-yl)-2-propyl-malonamide The title compound, MS: m/e=519.3 (M+H$^+$), was prepared in analogy to example 16 from 3-amino-1,3-dihydro-1-methyl-5-phenyl-2H-1,4-benzodiazepin-2-one and N-(3,5-difluoro-benzyl)-2-propyl-malonamic acid.

EXAMPLE 108

2-tert-Butyl-N-(3,5-difluoro-benzyl)-N'-(1-methyl-2-oxo-5-phenyl-2,3-dihydro-1H-benzo[e][1,4]diazepin-3-yl)-malonamide The title compound, MS: m/e=533.3 (M+H$^+$), was prepared in analogy to example 16 from 3-amino-1,3-dihydro-1-methyl-5-phenyl-2H-1,4-benzodiazepin-2-one and N-(3,5-difluoro-benzyl)-2-tert-butyl-malonamic acid.

EXAMPLE 109

N-(3,5-Difluoro-benzyl)-2-isopropyl-N'-(1-methyl-2-oxo-5-phenyl-2,3-dihydro-1H-benzo[e][1,4]diazepin-3-yl)-malonamide The title compound, MS: m/e=519.3 (M+H$^+$), was prepared in analogy to example 16 from 3-amino-1,3-dihydro-1-methyl-5-phenyl-2H-1,4-benzodiazepin-2-one and N-(3,5-difluoro-benzyl)-2-isopropyl-malonamic acid.

EXAMPLE 110

N-(3,5-Difluoro-benzyl)-2-ethyl-N'-(1-methyl-2-oxo-5-phenyl-2,3-dihydro-1H-benzo[e][1,4]diazepin-3-yl)-malonamide The title compound, MS: m/e=505.3 (M+H$^+$), was prepared in analogy to example 16 from 3-amino-1,3-dihydro-1-methyl-5-phenyl-2H-1,4-benzodiazepin-2-one and N-(3,5-difluoro-benzyl)-2-ethyl-malonamic acid.

EXAMPLE 111

N-(3,5-Difluoro-benzyl)-2-fluoro-N'-(1-methyl-2-oxo-5-phenyl-2,3-dihydro-1H-benzo[e][1,4]diazepin-3-yl)-malonamide The title compound, MS: m/e=495.3 (M+H$^+$), was prepared in analogy to example 16 from 3-amino-1,3-dihydro-1-methyl-5-phenyl-2H-1,4-benzodiazepin-2-one and N-(3,5-difluoro-benzyl)-2-fluoro-malonamic acid.

EXAMPLE 112

N-(3,5-Difluoro-benzyl)-2-methyl-N'-(5-methyl-6-oxo-6,7-dihydro-5H-dibenzo[b,d]azepin-7-yl)-malonamide The title compound, MS: m/e=464.3 (M+H$^+$), was prepared in analogy to example 16 from 7-amino-5-methyl-5H,7H-dibenzo[b,d]azepin-6-one.

EXAMPLE 113

N-(3,5-Difluoro-benzyl)-2-fluoro-2-methyl-N'-(5-methyl-6-oxo-6,7-dihydro-5H-dibenzo[b,d]azepin-7-yl)-malonamide The title compound, MS: m/e=482.3 (M+H$^+$), was prepared in analogy to example 16 from 7-amino-5-methyl-5H,7H-dibenzo[b,d]azepin-6-one and N-(3,5-difluoro-benzyl)-2-fluoro-2-methyl-malonamic acid.

EXAMPLE 114

N-(3,5-Difluoro-benzyl)-2-isopropyl-N'-(5-methyl-6-oxo-6,7-dihydro-5H-dibenzo[b,d]azepin-7-yl)-malonamide The title compound, MS: m/e=491.2 (M+H$^+$), was prepared in analogy to example 16 from 7-amino-5-methyl-5H,7H-dibenzo[b,d]azepin-6-one and N-(3,5-difluoro-benzyl)-2-isopropyl-malonamic acid.

EXAMPLE 115

N-(3,5-Difluoro-benzyl)-2-ethyl-N'-(5-methyl-6-oxo-6,7-dihydro-5H-dibenzo[b,d]azepin-7-yl)-malonamide The tide compound, MS: m/e=478.2 (M+H$^+$), was prepared in analogy to example 16 from 7-amino-5-methyl-5H,7H-dibenzo[b,d]azepin-6-one and N-(3,5-difluoro-benzyl)-2-ethyl-malonamic acid.

EXAMPLE 116

N-(3,5-Difluoro-benzyl)-2-fluoro-N'-(5-methyl-6-oxo-6,7-dihydro-5H-dibenzo[b,d]azepin-7-yl)-malonamide The title compound, MS: m/e=468.2 (M+H$^+$), was prepared in analogy to example 16 from 7-amino-5-methyl-5H,7H-dibenzo[b,d]azepin-6-one and N-(3,5-difluoro-benzyl)-2-fluoro-malonamic acid.

EXAMPLE 117

N-(3,5-Difluoro-benzyl)-2,2-dimethyl-N'-(5-methyl-6-oxo-6,7-dihydro-5H-dibenzo[b,d]azepin-7-yl)-malonamide The title compound, MS: m/e=478.2 (M+H$^+$), was prepared in analogy to example 16 from 7-amino-5-methyl-5H,7H-dibenzo[b,d]azepin-6-one and N-(3,5-difluoro-benzyl)-2,2-dimethyl-malonamic acid.

EXAMPLE 118

N-(3,5-Difluoro-benzyl)-N'-(5-methyl-6-oxo-6,7-dihydro-5H-dibenzo[b,d]azepin-7-yl)-2-propyl-malonamide The title compound, MS: m/e=492.3 (M+H$^+$), was prepared in analogy to example 16 from 7-amino-5-methyl-5H,7H-dibenzo[b,d]azepin-6-one and N-(3,5-difluoro-benzyl)-2-propyl-malonamic acid.

EXAMPLE 119

2-Benzyl-N-(3,5-difluoro-benzyl)-N'-(5-methyl-6-oxo-6,7-dihydro-5H-dibenzo[b,d]azepin-7-yl)-malonamide The title compound, MS: m/e=539.2 (M+H$^+$), was prepared in analogy to example 16 from 7-amino-5-methyl-5H,7H-dibenzo[b,d]azepin-6-one and N-(3,5-difluoro-benzyl)-2-benzyl-malonamic acid.

EXAMPLE 120

2-tert-Butyl-N-(3,5-difluoro-benzyl)-N'-(5-methyl-6-oxo-6,7-dihydro-5H-dibenzo[b,d]azepin-7-yl)-malonamide The title compound, MS: m/e=506.3 (M+H$^+$), was prepared in analogy to example 16 from 7-amino-5-methyl-5H,7H-dibenzo[b,d]azepin-6-one and N-(3,5-difluoro-benzyl)-2-tert-butyl-malonamic acid.

EXAMPLE 121

N-(3,5-Difluoro-benzyl)-N'-(5-methyl-6-oxo-6,7-dihydro-5H-dibenzo[b,d]azepin-7-yl)-malonamide The title compound, MS: m/e=450.2 (M+H$^+$), was prepared in analogy to example 16 from 7-amino-5-methyl-5H,7H-dibenzo[b,d]azepin-6-one and N-(3,5-difluoro-benzyl)-malonamic acid.

EXAMPLE 122

N-(4-Methoxy-benzyl)-2-methyl-N'-(5-methyl-6-oxo-6,7-dihydro-5H-dibenzo[b,d]azepin-7-yl)-malonamide a) N-(4-Methoxy-benzyl)-2-methyl-malonamic acid The title compound was prepared in analogy to N-(3,5-difluoro-benzyl)-2-methyl-malonamic acid (example 1).

b) N-(4-Methoxy-benzyl)-2-methyl-N'-(5-methyl-6-oxo-6,7-dihydro-5H-dibenzo[b,d]azepin-7-yl)-malonamide The title compound, MS: m/e=458.3 (M+H$^+$), was prepared in analogy to example 16 from 7-amino-5-methyl-5H,7H-dibenzo[b,d]azepin-6-one and N-(4-methoxy-benzyl)-2-methyl-malonamic acid.

EXAMPLE 123

N-Benzyl-2-methyl-N'-(5-methyl-6-oxo-6,7-dihydro-5H-dibenzo[b,d]azepin-7-yl)-malonamide a) N-Benzyl-2-methyl-malonamic acid The title compound was prepared in analogy to N-(3,5-difluoro-benzyl)-2-methyl-malonamic acid (example 1).

b) N-Benzyl-2-methyl-N'-(5-methyl-6-oxo-6,7-dihydro-5H-dibenzo[b,d]azepin-7-yl)-malonamide The title compound, MS: m/e=428.3 (M+H$^+$), was prepared in analogy to example 16 from 7-amino-5-methyl-5H,7H-dibenzo[b,d]azepin-6-one and N-benzyl-2-methyl-malonamic acid.

EXAMPLE 124

N-(3,4-Dimethoxy-benzyl)-2-methyl-N'-(5-methyl-6-oxo-6,7-dihydro-5H-dibenzo[b,d]azepin-7-yl)-malonamide a) N-(3,4-Dimethoxy-benzyl)-2-methyl-malonamic acid The title compound was prepared in analogy to N-(3,5-difluoro-benzyl)-2-methyl-malonamic acid (example 1).

b) N-(3,4-Dimethoxy-benzyl)-2-methyl-N'-(5-methyl-6-oxo-6,7-dihydro-5H-dibenzo[b,d]azepin-7-yl)-malonamide The title compound, MS: m/e=488.3 (M+H$^+$), was prepared in analogy to example 16 from 7-amino-5-methyl-5H,7H-dibenzo[b,d]azepin-6-one and N-(3,4-dimethoxy-benzyl)-2-methyl-malonamic acid.

EXAMPLE 125

N-(4-Fluoro-benzyl)-2-methyl-N'-(5-methyl-6-oxo-6,7-dihydro-5H-dibenzo[b,d]azepin-7-yl)-malonamide a) N-(4-Fluoro-benzyl)-2-methyl-malonamic acid The title compound was prepared in analogy to N-(3,5-difluoro-benzyl)-2-methyl-malonamic acid (example 1).

b) N-(4-Fluoro-benzyl)-2-methyl-N'-(5-methyl-6-oxo-6,7-dihydro-5H-dibenzo[b,d]azepin-7-yl)-malonamide The title compound, MS: m/e=446.2 (M+H$^+$), was prepared in analogy to example 16 from 7-amino-5-methyl-5H,7H-dibenzo[b,d]azepin-6-one and N-(4-fluoro-benzyl)-2-methyl-malonamic acid.

EXAMPLE 126

2-Methyl-N-(3-methyl-benzyl)-N'-(5-methyl-6-oxo-6,7-dihydro-5H-dibenzo[b,d]azepin-7-yl)-malonamide a) 2-Methyl-N-(3-methyl-benzyl)-malonamic acid The title compound was prepared in analogy to N-(3,5-difluoro-benzyl)-2-methyl-malonamic acid (example 1).

b) 2-Methyl-N-(3-methyl-benzyl)-N'-(5-methyl-6-oxo-6,7-dihydro-5H-dibenzo[b,d]azepin-7-yl)-malonamide The title compound, MS: m/e=442.3 (M+H$^+$), was prepared in analogy to example 16 from 7-amino-5-methyl-5H,7H-dibenzo[b,d]azepin-6-one and 2-methyl-N-(3-methyl-benzyl)-malonamic acid.

EXAMPLE 127

2-Methyl-N-(4-methyl-benzyl)-N'-(5-methyl-6-oxo-6,7-dihydro-5H-dibenzo[b,d]azepin-7-yl)-malonamide a) 2-Methyl-N-(4-methyl-benzyl)-malonamic acid The title compound was prepared in analogy to N-(3,5-difluoro-benzyl)-2-methyl-malonamic acid (example 1).

b) 2-Methyl-N-(4-methyl-benzyl)-N'-(5-methyl-6-oxo-6,7-dihydro-5H-dibenzo[b,d]azepin-7-yl)-malonamide The title compound, MS: m/e=441.2 (M+H$^+$), was prepared in analogy to example 16 from 7-amino-5-methyl-5H,7H-dibenzo[b,d]azepin-6-one and 2-methyl-N-(4-methyl-benzyl)-malonamic acid.

EXAMPLE 128

N-(4-Chloro-benzyl)-2-methyl-N'-(5-methyl-6-oxo-6,7-dihydro-5H-dibenzo[b,d]azepin-7-yl)-malonamide a) 2-Methyl-N-(4-chloro-benzyl)-malonamic acid The title compound was prepared in analogy to N-(3,5-difluoro-benzyl)-2-methyl-malonamic acid (example 1).

b) N-(4-Chloro-benzyl)-2-methyl-N'-(5-methyl-6-oxo-6,7-dihydro-5H-dibenzo[b,d]azepin-7-yl)-malonamide The title compound, MS: m/e=462.2 (M+H$^+$), was prepared in analogy to example 16 from 7-amino-5-methyl-5H,7H-dibenzo[b,d]azepin-6-one and 2-methyl-N-(4-chloro-benzyl)-malonamic acid.

EXAMPLE 129

N-(3,5-Dichloro-benzyl)-2-methyl-N'-(5-methyl-6-oxo-6,7-dihydro-5H-dibenzo[b,d]azepin-7-yl)-malonamide a) 2-Methyl-N-(3,5-dichloro-benzyl)-malonamic acid The title compound was prepared in analogy to N-(3,5-difluoro-benzyl)-2-methyl-malonamic acid (example 1).

b) N-(3,5-Dichloro-benzyl)-2-methyl-N'-(5-methyl-6-oxo-6,7-dihydro-5H-dibenzo[b,d]azepin-7-yl)-malonamide The title compound, MS: m/e=496.2 (M+H$^+$), was prepared in analogy to example 16 from 7-amino-5-methyl-5H,7H-dibenzo[b,d]azepin-6-one and 2-methyl-N-(3,5-dichloro-benzyl)-malonamic acid.

EXAMPLE 130

N-(3-Fluoro-benzyl)-2-methyl-N'-(5-methyl-6-oxo-6,7-dihydro-5H-dibenzo[b,d]azepin-7-yl)-malonamide a) 2-Methyl-N-(3-fluoro-benzyl)-malonamic acid
The title compound was prepared in analogy to N-(3,5-difluoro-benzyl)-2-methyl-malonamic acid (example 1).

b) N-(3-Fluoro-benzyl)-2-methyl-N'-(5-methyl-6-oxo-6,7-dihydro-5H-dibenzo[b,d]azepin-7-yl)-malonamide
The title compound, MS: m/e=446.2 (M+H$^+$), was prepared in analogy to example 16 from 7-amino-5-methyl-5H,7H-dibenzo[b,d]azepin-6-one and 2-methyl-N-(3-fluoro-benzyl)-malonamic acid.

EXAMPLE 131

N-(3,5-Dimethoxy-benzyl)-2-methyl-N'-(5-methyl-6-oxo-6,7-dihydro-5H-dibenzo[b,d]azepin-7-yl)-malonamide a) 2-Methyl-N-(3,5-dimethoxy-benzyl)-malonamic acid
The title compound was prepared in analogy to N-(3,5-difluoro-benzyl)-2-methyl-malonamic acid (example 1).

b) N-(3,5-Dimethoxy-benzyl)-2-methyl-N'-(5-methyl-6-oxo-6,7-dihydro-5H-dibenzo[b,d]azepin-7-yl)-malonamide
The title compound, MS: m/e=488.3 (M+H$^+$), was prepared in analogy to example 16 from 7-amino-5-methyl-5H,7H-dibenzo[b,d]azepin-6-one and 2-methyl-N-(3,5-dimethoxy-benzyl)-malonamic acid.

EXAMPLE 132

2-Methyl-N-(5-methyl-6-oxo-6,7-dihydro-5H-dibenzo[b,d]azepin-7-yl)-N'-(3-trifluoromethyl-benzyl)-malonamide a) 2-Methyl-N-(3-trifluoromethyl-benzyl)-malonamic acid
The title compound was prepared in analogy to N-(3,5-difluoro-benzyl)-2-methyl-malonamic acid (example 1).

b) 2-Methyl-N-(5-methyl-6-oxo-6,7-dihydro-5H-dibenzo[b,d]azepin-7-yl)-N'-(3-trifluoromethyl-benzyl)-malonamide
The title compound, MS: m/e=496.3 (M+H$^+$), was prepared in analogy to example 16 from 7-amino-5-methyl-5H,7H-dibenzo[b,d]azepin-6-one and 2-methyl-N-(3-trifluoromethyl-benzyl)-malonamic acid.

EXAMPLE 133

N-(2,5-Difluoro-benzyl)-2-methyl-N'-(5-methyl-6-oxo-6,7-dihydro-5H-dibenzo[b,d]azepin-7-yl)-malonamide a) 2-Methyl-N-(2,5-difluoro-benzyl)-malonamic acid
The title compound was prepared in analogy to N-(3,5-difluoro-benzyl)-2-methyl-malonamic acid (example 1).

b) N-(2,5-Difluoro-benzyl)-2-methyl-N'-(5-methyl-6-oxo-6,7-dihydro-5H-dibenzo[b,d]azepin-7-yl)-malonamide
The title compound, MS: m/e=464.2 (M+H$^+$), was prepared in analogy to example 16 from 7-amino-5-methyl-5H,7H-dibenzo[b,d]azepin-6-one and 2-methyl-N-(2,5-difluoro-benzyl)-malonamic acid.

EXAMPLE 134

2-Methyl-N-(5-methyl-6-oxo-6,7-dihydro-5H-dibenzo[b,d]azepin-7-yl)-N'-(2,3,5-trifluoro-benzyl)-malonamide a) 2-Methyl-N-(2,3,5-trifluoro-benzyl)-malonamic acid
The title compound was prepared in analogy to N-(3,5-difluoro-benzyl)-2-methyl-malonamic acid (example 1).

b) 2-Methyl-N-(5-methyl-6-oxo-6,7-dihydro-5H-dibenzo[b,d]azepin-7-yl)-N'-(2,3,5-trifluoro-benzyl)-malonamide
The title compound, MS: m/e=482.2 (M+H$^+$), was prepared in analogy to example 16 from 7-amino-5-methyl-5H,7H-dibenzo[b,d]azepin-6-one and 2-methyl-N-(2,3,5-trifluoro-benzyl)-malonamic acid.

EXAMPLE 135

N-(4-Methoxy-benzyl)-2-methyl-N'-(1-methyl-2-oxo-5-phenyl-2,3-dihydro-1H-benzo[e][1,4]diazepin-3-yl)-malonamide The title compound, MS: m/e=485.4 (M+H$^+$), was prepared in analogy to example 16 from 3-amino-1,3-dihydro-1-methyl-5-phenyl-2H-1,4-benzodiazepin-2-one and 2-methyl-N-(4-methoxy-benzyl)-malonamic acid.

EXAMPLE 136

N-Benzyl-2-methyl-N'-(1-methyl-2-oxo-5-phenyl-2,3-dihydro-1H-benzo[e][1,4]diazepin-3-yl)-malonamide The title compound, MS: m/e=455.3 (M+H$^+$), was prepared in analogy to example 16 from 3-amino-1,3-dihydro-1-methyl-5-phenyl-2H-1,4-benzodiazepin-2-one and 2-methyl-N-benzyl-malonamic acid.

EXAMPLE 137

N-(3,4-Dimethoxy-benzyl)-2-methyl-N'-(1-methyl-2-oxo-5-phenyl-2,3-dihydro-1H-benzo[e][1,4]diazepin-3-yl)-malonamide The title compound, MS: m/e=515.3 (M+H$^+$), was prepared in analogy to example 16 from 3-amino-1,3-dihydro-1-methyl-5-phenyl-2H-1,4-benzodiazepin-2-one and 2-methyl-N-(3,4-dimethoxy-benzyl)-malonamic acid.

EXAMPLE 138

N-(4-Fluoro-benzyl)-2-methyl-N'-(1-methyl-2-oxo-5-phenyl-2,3-dihydro-1H-benzo[e][1,4]diazepin-3-yl)-malonamide The title compound, MS: m/e=473.2 (M+H$^+$), was prepared in analogy to example 16 from 3-amino-1,3-dihydro-1-methyl-5-phenyl-2H-1,4-benzodiazepin-2-one and 2-methyl-N-(4-fluoro-benzyl)-malonamic acid.

EXAMPLE 139

2-Methyl-N-(4-methyl-benzyl)-N'-(1-methyl-2-oxo-5-phenyl-2,3-dihydro-1H-benzo[e][1,4]diazepin-3-yl)-malonamide The title compound, MS: m/e=468.2 (M+H$^+$), was prepared in analogy to example 16 from 3-amino-1,3-dihydro-1-methyl-5-phenyl-2H-1,4-benzodiazepin-2-one and 2-methyl-N-(4-methyl-benzyl)-malonamic acid.

EXAMPLE 140

2-Methyl-N-(3-methyl-benzyl)-N'-(1-methyl-2-oxo-5-phenyl-2,3-dihydro-1H-benzo[e][1,4]diazepin-3-yl)-malonamide The title compound, MS: m/e=468.2 (M+H$^+$), was prepared in analogy to example 16 from 3-amino-1,3-dihydro-1-methyl-5-phenyl-2H-1,4-benzodiazepin-2-one and 2-methyl-N-(3-methyl-benzyl)-malonamic acid.

EXAMPLE 141

N-(4-Chloro-benzyl)-2-methyl-N'-(1-methyl-2-oxo-5-phenyl-2,3-dihydro-1H-benzo[e][1,4]diazepin-3-yl)-malonamide The title compound, MS: m/e=489.3 (M+H$^+$), was prepared in analogy to example 16 from 3-amino-1,3-dihydro-1-methyl-5-phenyl-2H-1,4-benzodiazepin-2-one and 2-methyl-N-(4-chloro-benzyl)-malonamic acid.

EXAMPLE 142

N-(3,5-Dichloro-benzyl)-2-methyl-N'-(1-methyl-2-oxo-5-phenyl-2,3-dihydro-1H-benzo[e][1,4]diazepin-3-yl)-malonamide The title compound, MS: m/e=523.3 (M+H$^+$), was prepared in analogy to example 16 from 3-amino-1,3-dihydro-1-methyl-5-phenyl-2H-1,4-benzodiazepin-2-one and 2-methyl-N-(3,5-dichloro-benzyl)-malonamic acid.

EXAMPLE 143

N-(3-Fluoro-benzyl)-2-methyl-N'-(1-methyl-2-oxo-5-phenyl-2,3-dihydro-1H-benzo[e][1,4]diazepin-3-yl)-malonamide The title compound, MS: m/e=473.2 (M+H$^+$), was prepared in analogy to example 16 from 3-amino-1,3-dihydro-1-methyl-5-phenyl-2H-1,4-benzodiazepin-2-one and 2-methyl-N-(3-fluoro-benzyl)-malonamic acid.

EXAMPLE 144

N-(3,5-Dimethoxy-benzyl)-2-methyl-N'-(1-methyl-2-oxo-5-phenyl-2,3-dihydro-1H-benzo[e][1,4]diazepin-3-yl)-malonamide The title compound, MS: m/e=515.3 (M+H$^+$), was prepared in analogy to example 16 from 3-amino-1,3-dihydro-1-methyl-5-phenyl-2H-1,4-benzodiazepin-2-one and 2-methyl-N-(3,5-dimethoxy-benzyl)-malonamic acid.

EXAMPLE 145

2-Methyl-N-(1-methyl-2-oxo-5-phenyl-2,3-dihydro-1H-benzo[e][1,4]diazepin-3-yl)-N'-(3-trifluoromethyl-benzyl)-malonamide The title compound, MS: m/e=523.4 (M+H$^+$), was prepared in analogy to example 16 from 3-amino-1,3-dihydro-1-methyl-5-phenyl-2H-1,4-benzodiazepin-2-one and 2-methyl-N-(3-trifluoromethyl-benzyl)-malonamic acid.

EXAMPLE 146

N-(2,5-Difluoro-benzyl)-2-methyl-N'-(1-methyl-2-oxo-5-phenyl-2,3-dihydro-1H-benzo[e][1,4]diazepin-3-yl)-malonamide The title compound, MS: m/e=491.3 (M+H$^+$), was prepared in analogy to example 16 from 3-amino-1,3-dihydro-1-methyl-5-phenyl-2H-1,4-benzodiazepin-2-one and 2-methyl-N-(2,5-difluoro-benzyl)-malonamic acid.

EXAMPLE 147

2-Methyl-N-(1-methyl-2-oxo-5-phenyl-2,3-dihydro-1H-benzo[e][1,4]diazepin-3-yl)-N'-(2,3,5-trifluoro-benzyl)-malonamide The title compound, MS: m/e=509.3 (M+H$^+$), was prepared in analogy to example 16 from 3-amino-1,3-dihydro-1-methyl-5-phenyl-2H-1,4-benzodiazepin-2-one and 2-methyl-N-(2,3,5-trifluoro-benzyl)-malonamic acid.

EXAMPLE 148

N-{[(2-Benzyl-phenyl)-methyl-carbamoyl]-methyl}-N'-(3,5-difluoro-benzyl)-2-methyl-malonamide The title compound, MS: m/e=480.3 (M+H$^+$), was prepared in analogy to example 16 from 2-amino-2'-benzyl-N-methylacetanilide.

EXAMPLE 149

N-{[(4-Chloro-2-phenylsulfanyl-phenyl)-methyl-carbamoyl]-methyl}-N'-(3,5-difluoro-benzyl)-2-methyl-malonamide The title compound, MS: m/e=533.4 (M+H$^+$), was prepared in analogy to example 16 from 2-amino-4'-chloro-N-methyl-2'-(phenylthio)acetanilide.

EXAMPLE 150

N-{[(2-Benzoyl-4-chloro-phenyl)-methyl-carbamoyl]-methyl}-N'-(3,5-difluoro-benzyl)-2-methyl-malonamide The title compound, MS: m/e=528.4 (M+H$^+$), was prepared in analogy to example 16 from 2-amino-2'-benzoyl-4'-chloro-N-methylacetanilide.

EXAMPLE 151

N-(2-Fluoro-benzyl)-2-methyl-N'-(5-methyl-6-oxo-6,7-dihydro-5H-dibenzo[b,d]azepin-7-yl)-malonamide a) 2-Methyl-N-(5-methyl-6-oxo-6,7-dihydro-5H-dibenzo[b,d]azepin-7-yl)-malonamic acid tert-butyl ester To a cooled solution (0° C.) of 2-methyl-malonic acid mono-tert-butyl ester (1.01 g, 5.79 mmol) and 7-amino-5-methyl-5H,7H-dibenzo[b,d]azepin-6-one (1.15 g, 4.83 mmol) in THF (8 ml) was added hydroxybenzotriazole (652 mg, 4.83 mmol), diisopropylethylamine (624 mg, 4.83 mmol) and N-(3-dimethylaminopropyl)-N'-ethylcarbodiimide hydrochloride (925 mg, 4.83 mmol), and the mixture was stirred overnight at r.t. The solvent was evaporated, the residue was taken up in ethyl acetate, washed with water, and dried ($Na_2SO_4$). After evaporation of the solvent, the title compound, MS: m/e=395.3 (M+H+), (920 mg, 48%) was obtained by chromatographic purification of the residue (silica gel, MeOH, CH2Cl2).

b) 2-Methyl-N-(5-methyl-6-oxo-6,7-dihydro-5H-dibenzo[b,d]azepin-7-yl)-malonamic acid TFA (3 ml) was added to a solution of 2-methyl-N-(5-methyl-6-oxo-6,7-dihydro-5H-dibenzo[b,d]azepin-7-yl)-malonamic acid tert-butyl ester (920 mg, 2.33 mmol) in dichloromethane (3 ml) and the mixture was stirred at r.t. overnight. The mixture was then taken up in more dichloromethane, washed with water, and dried ($Na_2SO_4$). After evaporation of the solvent, the title compound, MS: m/e=339.3 (M+H+), (580 mg, 73%) was obtained by chromatographic purification of the residue (silica gel, MeOH, $CH_2Cl_2$).

c) N-(2-Fluoro-benzyl)-2-methyl-N'-(5-methyl-6-oxo-6,7-dihydro-5H-dibenzo[b,d]azepin-7-yl)-malonamide 2-Methyl-N-(5-methyl-6-oxo-6,7-dihydro-5H-dibenzo[b,d]azepin-7-yl)-malonamic acid (20 mg, 0.059 mmol) and 2-fluorobenzylamine (7.4 mg, 0.059 mmol) were placed in a disposable polypropylene tube and dissolved in DMF (2 ml). TPTU (2-(2-pyridon-1-yl)-1,1,3,3-tetramethyl uronium tetrafluoroborate, 19 mg, 0.065 mmol) was added, and the mixture was shaken overnight at r.t. The title compound, MS: m/e=446.2 (M+H+), was isolated from the reaction mixture by automated, preparative HPLC (YMC CombiPrep C18 column 50×20 mm, solvent gradient 5-95% $CH_3CN$ in 0.1% TFA(aq) over 6.0 min, λ=230 nm, flow rate 40 ml/min).

EXAMPLE 152

N-(2-Chloro-benzyl)-2-methyl-N'-(5-methyl-6-oxo-6,7-dihydro-5H-dibenzo[b,d]azepin-7-yl)-malonamide The title compound, MS: m/e=462.2 (M+H+), was prepared in analogy to example 151 from 2-chlorobenzylamine.

EXAMPLE 153

2-Methyl-N-(2-methyl-benzyl)-N'-(5-methyl-6-oxo-6,7-dihydro-5H-dibenzo[b,d]azepin-7-yl)-malonamide The title compound, MS: m/e=442.3 (M+H+), was prepared in analogy to example 151 from 2-methylbenzylamine.

EXAMPLE 154

N-(2-Methoxy-benzyl)-2-methyl-N'-(5-methyl-6-oxo-6,7-dihydro-5H-dibenzo[b,d]azepin-7-yl)-malonamide The title compound, MS: m/e=458.3 (M+H+), was prepared in analogy to example 151 from 2-methoxybenzylamine.

EXAMPLE 155

2-Methyl-N-(5-methyl-6-oxo-6,7-dihydro-5H-dibenzo[b,d]azepin-7-yl)-N'-(2-trifluoromethyl-benzyl)-malonamide The title compound, MS: m/e=496.3 (M+H+), was prepared in analogy to example 151 from 2-trifluoromethyl-benzylamine.

EXAMPLE 156

N-(3-Methoxy-benzyl)-2-methyl-N'-(5-methyl-6-oxo-6,7-dihydro-5H-dibenzo[b,d]azepin-7-yl)-malonamide The title compound, MS: m/e=458.3 (M+H+), was prepared in analogy to example 151 from 3-methoxybenzylamine.

EXAMPLE 157

N-(3-Chloro-benzyl)-2-methyl-N'-(5-methyl-6-oxo-6,7-dihydro-5H-dibenzo[b,d]azepin-7-yl)-malonamide The title compound, MS: m/e=462.2 (M+H+), was prepared in analogy to example 151 from 3-chlorobenzylamine.

EXAMPLE 158

2-Methyl-N-(5-methyl-6-oxo-6,7-dihydro-5H-dibenzo[b,d]azepin-7-yl)-N'-(4-trifluoromethyl-benzyl)-malonamide The title compound, MS: m/e=496.3 (M+H$^+$), was prepared in analogy to example 151 from 4-trifluorobenzylamine.

EXAMPLE 159

N-(3,5-Difluoro-benzyl)-2-methoxy-N'-(5-methyl-6-oxo-6,7-dihydro-5H-dibenzo[b,d]azepin-7-yl)-malonamide The title compound, MS: m/e=480.2 (M+H$^+$), was prepared in analogy to example 16 from 7-amino-5-methyl-5H,7H-dibenzo[b,d]azepin-6-one and N-(3,5-difluoro-benzyl)-2-methoxy-malonamic acid.

EXAMPLE 160

(2S-cis)-N-(2-Carbamoyl-4-oxo-1,2,4,5,6,7-hexahydro-azepino[3,2,1-hi]indol-5-yl)-N'-(3,5-difluoro-benzyl)-(2R,S)-methyl-malonamide Solid phase synthesis was performed on a benzhydrylamine polystyrene resin, functionalized with an Fmoc-amide linker, p-[(R,S)-a-1-(9H-fluoren-9-yl)methoxyformamido-2,4-dimethoxybenzyl]phenoxyacetic acid. The functionalized resin (300 mg., 0.6 mmol/g loading ) was treated with 20% piperidine/DMF (10 ml, 10 min) and then washed (3×alternating DMF/isopropanol). (2S-cis)-5-(9H-fluoren-9-yl)methoxycarbonylamino-4-oxo-1,2,4,5,6,7-hexahydro-azepono[3,2,1-hi]indole-2-carboxylic (127 mg, 0.27 mmol), O-(1,2-dihydro-2-oxopyridyl-1-yl)-N,N,N',N'-tetramethyluroniumtetrafluoroborate (TPTU) (80 mg, 0.41 mmol), diisopropylethylamine (140 µl, 1.22 mmol) and DMF (5 ml) were added to the resin. The mixture was shaken for 1 h. (Ninhydrin test: negative) and the resin was filtered and washed as above. (131 mg, 0.54 mmol), TPTU (160 mg, 0.54 mmol), diisopropylethylamine (280 µl, 1.62 mmol) and DMF (5 ml) were added to the resin and coupled as above. Product was cleaved from the resin using 90% TFA aqueous (5 ml) for 1 h. The filtrate was concentrated under reduced pressure and purified by prep. RP(C18) HPLC. Desired fractions were pooled and lyophilized: 30 mg, MS: 471.2 (MH$^+$ (60%)), 493.1 (MNa$^+$ (100), 426.3 (MH$^+$–CONH$_2$);

EXAMPLE 161

(2S-cis)-N-(2-Cyano-4-oxo-1,2,4,5,6,7-hexahydro-azepino[3,2,1-hi]indol-5-yl)-N'-(3,5-difluoro-benzyl)-(2R,S)-methyl-malonamide A mixture containing (2S-cis)-N-(2-carbamoyl-4-oxo-1,2,4,5,6,7-hexahydro-azepino[3,2,1-hi]indol-5-yl)-N'-(3,5-difluoro-benzyl)-(2R,S)-methyl-malonamide (18.5 mg, 0.04 mmol), methoxycarbonylsulfamoyl-triethylammonium hydroxide (Burgess reagent) (19 mg, 0.08 mmol) in THF (1.5 ml) was shaken for 30 h at 70° C. under an argon atmosphere. The reaction mixture was concentrated under reduced pressure and ethyl acetate was added. The organic phase was washed with water, dried (Na$_2$SO$_4$), filtered and concentrated under reduced pressure. Purification by prep.RP(C18)HPLC: 10 mg, MS: 530.1 (MH+(100%)), 552.1 (MNa+(30));

EXAMPLE 162

(2S-cis)-N-(3,5-Difluoro-benzyl)-2-methyl-N'-{4-oxo-2-[(2-thiophen-2-yl-acetylamino)-(2R,S)-methyl]-1,2,4,5,6,7-hexahydro-azepino[3,2,1-hi]indol-5-yl}-malonamide a) (2S-cis)-(2-Cyano-4-oxo-1,2,4,5,6,7-hexahydro-azepino[3,2,1-hi]indol-5-yl)-carbamic acid tert-butyl ester 9-Fmoc-aminoxanthen-3-yloxy-methyl resin (Sieber Amide resin; Calbiochem-Novabiochem AG) (5 g, 0.52 mmol/g loading) was treated with 20% piperidine/DMF (50 ml, 10 min) and then washed (3×alternating DMF/isopropanol). (2S-cis)-5-(9H-Fluoren-9-yl)methoxycarbonylamino-4-oxo-1,2,4,5,6,7-hexahydro-azepino[3,2,1-hi]indole-2-carboxylic (1.83 g, 3.9 mmol), TPTU (1.2 g, 3.9 mmol), diisopropylethylamine (3 ml, 17.6 mmol) and DMF (10 ml) were added to the resin. Coupling was allowed to proceed for 1 h (Ninhydrin test: negative) and the resin was filtered and washed as before. Fmoc group removal was followed by t-Boc group amine protection using t-Boc anhydride (5.7 g, 26 mmol) diisopropylethylamine (2.2 ml, 13 mmol) in 12 ml dichloromethane. The washed, dried resin was treated with trifluoroacetic anhydride (1.8 ml, 13 mmol), pyridine (2.1 ml, 26 mmol) in 15 ml dichloromethane for 16 h at room temperature. The filtrate was collected and the resin washed (CH$_2$Cl$_2$, 2×10 ml). The combined organic fractions were washed with 5% NaHCO$_3$, dried (MgSO$_4$) filtered and concentrated under reduced pressure yielding a crude oil which was purified by flash chromatography (ethyl acetate-n-hexanes 1:3): 0.71 g; MS: 328.3 (MH$^+$(20%)); 228.2 (MH$^+$-Boc(100)).

b) (2S-cis)-{4-Oxo-2-[(2-thiophen-2-yl-acetylamino)-methyl]-1,2,4,5,6,7-hexahydro-azepino[3,2,1-hi]indol-5-yl}-carbamic acid tert-butyl ester (2S-cis)-(2-Cyano-4-oxo-1,2,4,5,6,7-hexahydro-azepino[3,2,1-hi]indol-5-yl)-carbamic acid tert-butyl ester (0.59 g, 1.80 mmol) was hydrogenated over palladium on carbon (10%, 0.22 g) in 80 ml acetic acid for 1 h. The mixture was filtered (Decalite) and the filtrate was lyophilized: 0.33 g white solid. A part of this lyophilisate (0.16 g, 0.48 mmol) was dissolved in 8 ml DMF and was coupled to thiophene-2-acetic acid (0.21 g, 1.45 mmol) in the presence of TPTU (0.43 g, 1.45 mmol), diisopropylethylamine (0.84 ml, 5 mmol) for 1 h. The reaction mixture was concentrated under reduced pressure and the residue was dissolved in ethyl acetate and washed successively with 1N NaHCO$_3$, 0.2 N KHSO$_4$, water and the organic phase was dried (MgSO$_4$) filtered and concentrated under reduced pressure, Purification by flash chromatgraphy (ethyl acetate.n.hexanes 3:1): white foam, 125 mg; MS: 456.3 (MH$^+$(60%)).

c) (2S-cis)-N-(3,5-Difluoro-benzyl)-2-methyl-N'-{4-oxo-2-[(2-thiophen-2-yl-acetylamino)-(2R,S)-methyl]-1,2,4,5,6,7-hexahydro-azepino[3,2,1-hi]indol-5-yl}-malonamide (2S-cis)-{4-Oxo-2-[(2-thiophen-2-yl-acetylamino)-methyl]-1,2,4,5,6,7-hexahydro-azepino[3,2,1-hi]indol-5-yl}-carbamic acid tert-butyl ester was treated with 4 M HCl/1,4-dioxan (3 ml) for 1 h at room temperature and the reaction mixture was concentrated under reduced pressure and concentrated another two times from acetonitrile. The hydrochloride salt (ca. 20 mg) was dissolved in 1 ml DMF and the pH of the solution was adjusted to 8. Malonic acid derivative, (41 mg, 0.17 mmol) TPTU (50 mg, 0.17 mmol) diisopropylethylamine (87 µl, 0.51 mmol) in 0,5 ml DMF were added and the reaction mixture was shaken for 1 h. The reaction mixture was acidified with acetic acid, concentrated to a smaller volume and directly purified by prep.RP(Cl8) HPLC: 14.5 mg, MS: 581.1 (MH$^+$(100%));

EXAMPLE 163

(2S-cis)-N-(3,5-Difluoro-benzyl)-N'-(2-{[2-(4-fluoro-phenyl)-acetylamino]-methyl}-4-oxo-1,2,4,5,6,7-hexahydro-azepino[3,2,1-hi]indol-5-yl)-(2R,S)-methyl-malonamide The title compound was obtained in comparable yields according to the procedures described for example 162 using 4-fluorophenylacetic acid instead of thiophene-2-acetic acid: 15.8 mg, MS: 593.2 (MH$^+$(100%));

EXAMPLE 164

(2S-cis)-N-(3,5-Difluoro-benzyl)-2,2-dimethyl-N'-{4-oxo-2-[(2-thiophen-2-yl-acetylamino)-methyl]-1,2,4,5,6,7-hexahydro-azepino[3,2,1-hi]indol-5-yl}-malonamide The title compound was obtained in comparable yields according to the procedures described for example 162 using malonic acid derivative N-(3,5-difluorobenzyl)-2,2-dimethyl-malonamic acid instead of derivative N-(3,5-difluorobenzyl)-2-methyl-malonamic acid: 15.0 mg, MS: 595.1 (MH$^+$(100%));

EXAMPLE 165

(2S-cis)-N-(3,5-Difluoro-benzyl)-N'-(2-{[2-(4-fluoro-phenyl)-acetylamino]-methyl}-4-oxo-1,2,4,5,6,7-hexahydro-azepino[3,2,1-hi]indol-5-yl)-2,2-dimethyl-malonamide The title compound was obtained in comparable yields according to the procedures described for example 162 using 4-fluorophenylacetic acid instead of thiophene-2-acetic acid and malonic acid derivative N-(3,5-difluorobenzyl)-2,2-dimethyl-malonamic acid instead of N-(3,5-difluorobenzyl)-2-methyl-malonamic acid: 5.4 mg, MS: 607.1 (MH$^+$(100

EXAMPLE 166

2-Methyl-N-(5-methyl-6-oxo-6,7-dihydro-5H-dibenzo[b,d]azepin-7-yl)-N'-phenyl-malonamide a) 2-Methyl-N-(5-methyl-6-oxo-6,7-dihydro-5H-dibenzo[b,d]azepin-7-yl)-malonamic acid tert-butyl ester To a cooled solution (0° C.) of 2-methyl-malonic acid mono-tert-butyl ester (1.01 g, 5.79 mmol) and 7-amino-5-methyl-5H,7H-dibenzo[b,d]azepin-6-one (1.15 g, 4.83 mmol) in THF (8 ml) was added hydroxybenzotriazole (652 mg, 4.83 mmol), diisopropylethylamine (624 mg, 4.83 mmol)and N-(3-dimethylaminopropyl)-N'-ethylcarbodiimide hydrochloride (925 mg, 4.83 mmol), and the mixture was stirred overnight at r.t. The solvent was evaporated, the residue was taken up in ethyl acetate, washed with water, and dried (Na$_2$SO$_4$). After evaporation of the solvent, the title compound, MS: m/e=395.3 (M+H$^+$), (920 mg, 48%) was obtained by chromatographic purification of the residue (silica gel, MeOH, CH$_2$Cl$_2$).

b) 2-Methyl-N-(5-methyl-6-oxo-6,7-dihydro-5H-dibenzo[b,d]azepin-7-yl)-malonamic acid TFA (3 ml) was added to a solution of 2-methyl-N-(5-methyl-6-oxo-6,7-dihydro-5H-dibenzo[b,d]azepin-7-yl)-malonamic acid tert-butyl ester (920 mg, 2.33 mmol) in dichloromethane (3 ml) and the mixture was stirred at r.t. overnight. The mixture was then taken up in more dichloromethane, washed with water, and dried (Na$_2$SO$_4$). After evaporation of the solvent, the title compound, MS: m/e=339.3 (M+H$^+$), (580 mg, 73%) was obtained by chromatographic purification of the residue (silica gel, MeOH, CH$_2$Cl$_2$).

c) 2-Methyl-N-(5-methyl-6-oxo-6,7-dihydro-5H-dibenzo[b,d]azepin-7-yl)-N'-phenyl-malonamide 2-Methyl-N-(5-methyl-6-oxo-6,7-dihydro-5H-dibenzo[b,d]azepin-7-yl)-malonamic acid (20 mg, 0.059 mmol) and aniline (6 mg, 0.059 mmol) were placed in a disposable polypropylene tube and dissolved in DMF (2 ml). TPTU (2-(2-pyridon-1-yl)-1,1,3,3-tetramethyl uronium tetrafluoroborate, 19 mg, 0.065 mmol) was added, and the mixture was shaken overnight at r.t. The title compound, MS: m/e=414.2 (M+H$^+$), was isolated from the reaction mixture by automated, preparative HPLC (YMC CombiPrep C18 column 50×20 mm, solvent gradient 5-95% CH$_3$CN in 0.1% TFA(aq) over 6.0 min, λ=230 nm, flow rate 40 ml/min).

EXAMPLE 167

2-Methyl-N-(5-methyl-6-oxo-6,7-dihydro-5H-dibenzo[b,d]azepin-7-yl)-N'-phenethyl-malonamide The title compound, MS: m/e=442.3 (M+H$^+$), was prepared in analogy to example 166 from 2-phenethylamine.

EXAMPLE 168

N-[2-(4-Fluoro-phenyl)-ethyl]-2-methyl-N'-(5-methyl-6-oxo-6,7-dihydro-5H-dibenzo[b,d]azepin-7-yl)-malonamide The title compound, MS: m/e=460.3 (M+H$^+$), was prepared in analogy to example 166 from 4-fluorophenethylamine.

EXAMPLE 169

N-[2-(4-Chloro-phenyl)-ethyl]-2-methyl-N'-(5-methyl-6-oxo-6,7-dihydro-5H-dibenzo[b,d]azepin-7-yl)-malonamide The title compound, MS: m/e=476.2 (M+H$^+$), was prepared in analogy to example 166 from 4-chlorophenethylamine.

EXAMPLE 170

N-[2-(3-Fluoro-phenyl)-ethyl]-2-methyl-N'-(5-methyl-6-oxo-6,7-dihydro-5H-dibenzo[b,d]azepin-7-yl)-malonamide The title compound, MS: m/e=460.3 (M+H$^+$), was prepared in analogy to example 166 from 3-fluorophenethylamine.

EXAMPLE 171

2-Methyl-N-(5-methyl-6-oxo-6,7-dihydro-5H-dibenzo[b,d]azepin-7-yl)-N'-pyridin-3-ylmethyl-malonamide The title compound, MS: m/e=429.3 (M+H$^+$), was prepared in analogy to example 166 from 3-aminomethylpyridine.

EXAMPLE 172

2-Methyl-N-(5-methyl-6-oxo-6,7-dihydro-5H-dibenzo[b,d]azepin-7-yl)-N'-pyridin-2-ylmethyl-malonamide The title compound, MS: m/e=429.3 (M+H$^+$), was prepared in analogy to example 166 from 2-aminomethylpyridine.

EXAMPLE 173

N-Furan-2-ylmethyl-2-methyl-N'-(5-methyl-6-oxo-6,
7-dihydro-5H-dibenzo[b,d]azepin-7-yl)-malonamide The tide compound, MS: m/e=418.3 (M+H$^+$), was prepared in analogy to example 166 from 2-aminomethylfurane.

EXAMPLE 174

2-Methyl-N-(5-methyl-6-oxo-6,7-dihydro-5H-
dibenzo[b,d]azepin-7-yl)-N'-pyridin-4-ylmethyl-
malonamide The tide compound, MS: m/e=429.3 (M+H$^+$), was prepared in analogy to example 166 from 4-aminomethylpyridine.

EXAMPLE 175

2-Methyl-N-(5-methyl-furan-2-ylmethyl)-N'-(5-methyl-6-oxo-6,7-dihydro-5H-dibenzo[b,d]azepin-7-
yl)-malonamide The title compound, MS: m/e=432.3 (M+H$^+$), was prepared in analogy to example 166 from 5-methylfurfurylamine.

EXAMPLE 176

N-Benzo[b]thiophen-3-ylmethyl-2-methyl-N'-(5-
methyl-6-oxo-6,7-dihydro-5H-dibenzo[b,d]azepin-7-
yl)-malonamide The title compound, MS: m/e=484.3 (M+H$^+$), was prepared in analogy to example 166 from 3-aminomethylbenzothiophene.

EXAMPLE 177

2-Methyl-N-(5-methyl-6-oxo-6,7-dihydro-5H-
dibenzo[b,d]azepin-7-yl)-N'-(1-phenyl-ethyl)-malonamide The title compound, MS: m/e=442.3 (M+H$^+$), was prepared in analogy to example 166 from (R)-(+)-1-phenylethylamine.

EXAMPLE 178

2-Methyl-N-(5-methyl-6-oxo-6,7-dihydro-5H-
dibenzo[b,d]azepin-7-yl)-N'-(2-hydroxyethyl)-malonamide The title compound, MS: m/e=472.3 (M+H$^+$), was prepared in analogy to example 166 from N-benzylethanolamine.

EXAMPLE 179

2-Methyl-N-(5-methyl-6-oxo-6,7-dihydro-5H-
dibenzo[b,d]azepin-7-yl)-N'-benzyl-N'-methyl-malonamide The title compound, MS: m/e=442.3 (M+H$^+$), was prepared in analogy to example 166 from N-methylbenzylamine.

EXAMPLE 180

2-Methyl-N-(5-methyl-6-oxo-6,7-dihydro-5H-
dibenzo[b,d]azepin-7-yl)-N'-benzyl-N'-(2-cyanoethyl)-malonamide The title compound, MS: m/e=481.3 (M+H$^+$), was prepared in analogy to example 166 from N-benzyl-aminoacetonitrile.

EXAMPLE 181

2-Methyl-N-(5-methyl-6-oxo-6,7-dihydro-5H-
dibenzo[b,d]azepin-7-yl)-N'-(1,2,3,4-tetrahydro-
naphthalen-1-yl)-malonamide The title compound, MS: m/e=468.3 (M+H$^+$), was prepared in analogy to example 166 from 1,2,3,4-tetrahydro-naphthalen-1-yl-amine.

EXAMPLE 182

2-Methyl-N-(5-methyl-6-oxo-6,7-dihydro-5H-
dibenzo[b,d]azepin-7-yl)-N'-(indane-1-yl)-malonamide The title compound, MS: m/e=454.3 (M+H$^+$), was prepared in analogy to example 166 from 1-aminoindane.

EXAMPLE 183

N-(4,6-Difluoro-indan-1-yl)-2-methyl-N'-(5-methyl-
6-oxo-6,7-dihydro-5H-dibenzo[b,d]azepin-7-yl)-
malonamide The title compound, MS: m/e=490.3 (M+H$^+$), was prepared in analogy to example 166 from 4,6-difluoro-1-aminoindane.

EXAMPLE 184

N-(1-Hydroxy-indan-2-yl)-2-methyl-N'-(5-methyl-6-
oxo-6,7-dihydro-5H-dibenzo[b,d]azepin-7-yl)-malonamide The title compound, MS: m/e=470.4 (M+H$^+$), was prepared in analogy to example 166 from 2-amino-1-indanol.

EXAMPLE 185

N-Indan-2-yl-2-methyl-N'-(5-methyl-6-oxo-6,7-di-
hydro-5H-dibenzo[b,d]azepin-7-yl)-malonamide The title compound, MS: m/e=454.3 (M+H$^+$), was prepared in analogy to example 166 from 2-aminoindane.

EXAMPLE 186

N-(2,2-Difluoro-1-phenyl-cyclopropylmethyl)-2-
methyl-N'-(5-methyl-6-oxo-6,7-dihydro-5H-dibenzo
[b,d]azepin-7-yl)-malonamide The title compound, MS: m/e=504.3 (M+H$^+$), was prepared in analogy to example 166 from C-(2,2-difluoro-1-phenyl-cyclopropyl)-methylamine.

EXAMPLE 187

N-(2,2-Dimethyl-[1,3]dioxolan-4-ylmethyl)-2-methyl-N'-(5-methyl-6-oxo-6,7-dihydro-5H-dibenzo[b,d]azepin-7-yl)-malonamide The title compound, MS: m/e=450.3 (M–H+), was prepared in analogy to example 166 from (RS)-2,2-dimethyl-[1,3]dioxolan-4-ylmethylamine.

EXAMPLE 188

2-Methyl-N-(5-methyl-6-oxo-6,7-dihydro-5H-dibenzo[b,d]azepin-7-yl)-N'-(tetrahydro-furan-2-ylmethyl)-malonamide The title compound, MS: m/e=420.2 (M–H+), was prepared in analogy to example 166 from (RS)-tetrahydro-furan-2-ylmethylamine.

EXAMPLE A

Tablet Formulation (Wet Granulation)

| Item | Ingredients | 5 mg | 25 mg | 100 mg | 500 mg |
|---|---|---|---|---|---|
| | | mg/tablet | | | |
| 1. | Compound of formula IA or IB | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4 | Microcrystalline Cellulose | 30 | 30 | 30 | 150 |
| 5 | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

EXAMPLE B

Capsule Formulation

| Item | Ingredients | 5 mg | 25 mg | 100 mg | 500 mg |
|---|---|---|---|---|---|
| | | mg/capsule | | | |
| 1. | Compound of formula IA or IB | 5 | 25 | 100 | 500 |
| 2. | Hydrous Lactose | 159 | 123 | 148 | — |
| 3. | Corn Starch | 25 | 35 | 40 | 70 |
| 4 | Talc | 10 | 15 | 10 | 25 |
| 5 | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

The invention claimed is:
1. A compound of formula

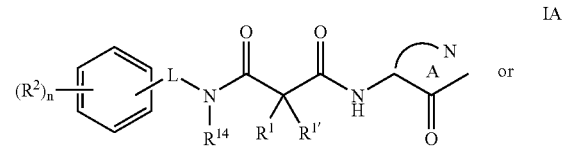

IA

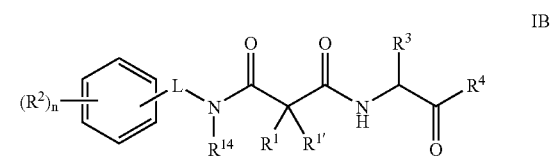

IB wherein

L is a bond, —$(CH_2)_m$—, —$CH(CH_3)$—, or is

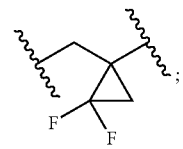

$R^1$ and $R^{1'}$ are the same or different and are hydrogen, lower alkyl, halogen, benzyl or lower alkenyl;

each $R^2$ is independently selected from the group consisting of hydrogen, hydroxy, halogen, lower alkyl, lower alkoxy and trifluoromethyl;

$R^3$ is phenyl or benzyl, each of which is unsubstituted or substituted by one or two substituents selected from the group consisting of halogen and cyano, or is
lower alkyl,
two hydrogen atoms,
$(CH_2)_m$—S-lower alkyl,
$(CH_2)_m$-cycloalkyl,
$(CH_2)_m$—OH,
$CH_2OCH_2$-phenyl,

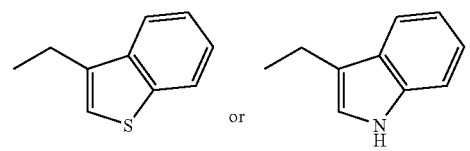

$R^4$ is lower alkoxy,
mono- or dialkyl amino,
$N(CH_3)(CH_2)_m$—C≡CH,
or is a mono-, di or tricyclic group, unsubstituted or substituted by $R^5$ to $R^{10}$, and
which groups can be linked by —$N(CH_3)(CH_2)_o$- to the —C(O)-group in formula IB, selected from the group consisting of

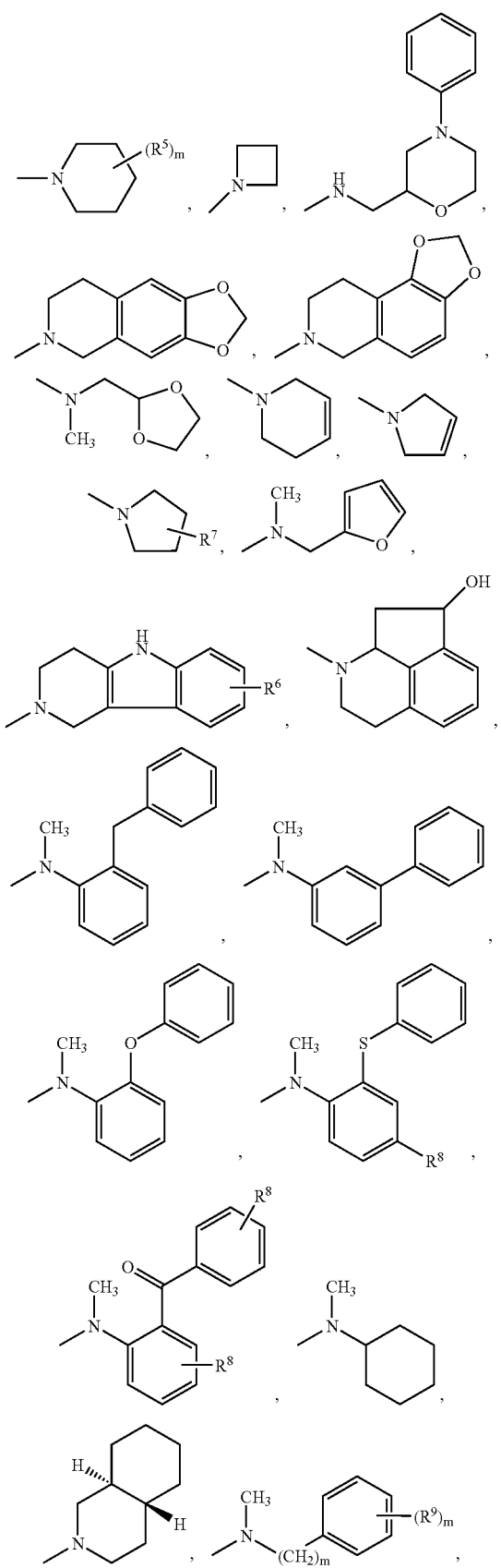

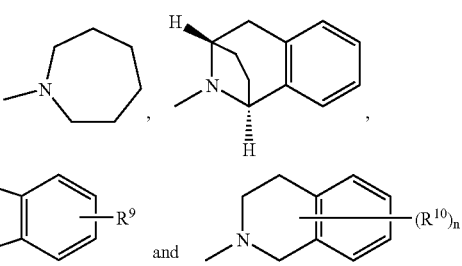

wherein each $R^5$ is independently selected from the group consisting of hydrogen, halogen, lower alkyl and —$(CH_2)_mOH$;

$R^6$ hydrogen, halogen or lower alkoxy;

$R^7$ is hydrogen or —$CH_2OCH_3$;

$R^8$ is hydrogen or halogen;

$R^9$ is hydrogen, lower alkoxy, lower alkyl or amino;

each $R^{10}$ is independently selected from the group consisting of hydrogen, lower alkyl, lower alkoxy, lower cycloalkyl, halogen, hydroxy, =O, amino, nitro, —$CH_2CN$,

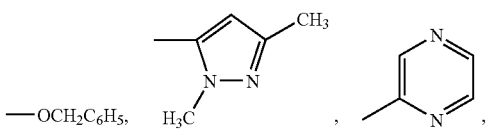

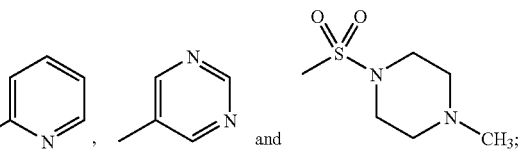

m is 1 or 2;

n is 1, 2 or 3;

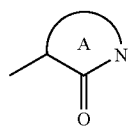

is selected from the group consisting of

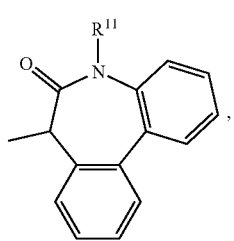

a)

-continued b) 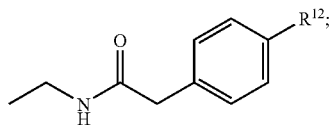

R¹⁴ is hydrogen, lower alkyl, —(CH₂)₂OH or —(CH₂)₂CN;

or a pharmaceutically acceptable acid addition salt thereof.

2. A compound of formula

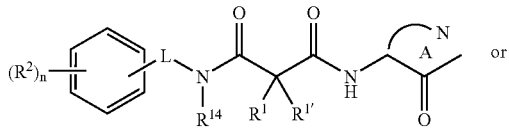

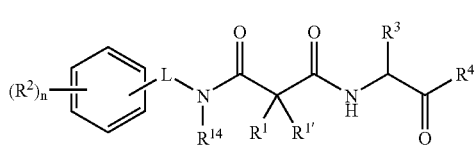

wherein

R¹ and R¹' are the same or different and are hydrogen, lower alkyl, halogen, benzyl or lower alkenyl;

each R² is independently selected from the group consisting of hydrogen, halogen, lower alkyl, lower alkoxy and trifluoromethyl;

R³ is phenyl or benzyl, each of which is unsubstituted or substituted by one or two substituents selected from the group consisting of halogen and cyano, or is lower alkyl, two hydrogen atoms, (CH₂)ₘ—S-lower alkyl, (CH₂)ₘ-cycloalkyl, (CH₂)ₘ-OH, CH₂OCH₂-phenyl,

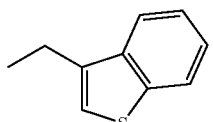 or 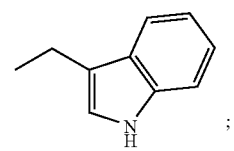 ;

R⁴ is lower alkoxy, mono- or dialkyl amino,

N(CH₃)(CH₂)ₘ—C≡CH, or is a mono-, di or tricyclic group, unsubstituted or substituted by R⁵ to R¹⁰, and which groups can be linked by —N(CH₃)(CH₂)ₒ- to the —C(O)-group in formula IB, selected from the group consisting of

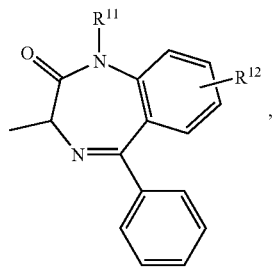

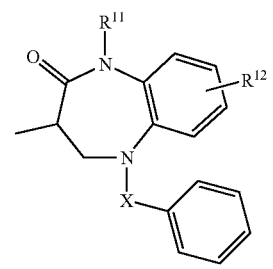

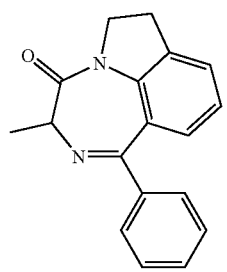

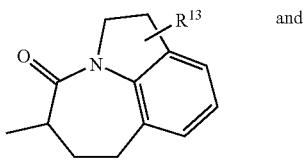

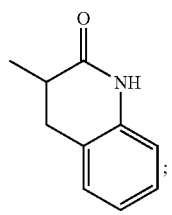

wherein

X is —CH₂, —S(O)₂ or —C(O)—;

R¹¹ is hydrogen or lower alkyl;

R¹² is hydrogen or halogen;

R¹³ is hydrogen, CN, hydroxy, —C(O)NH₂,

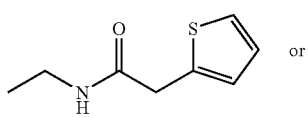 or

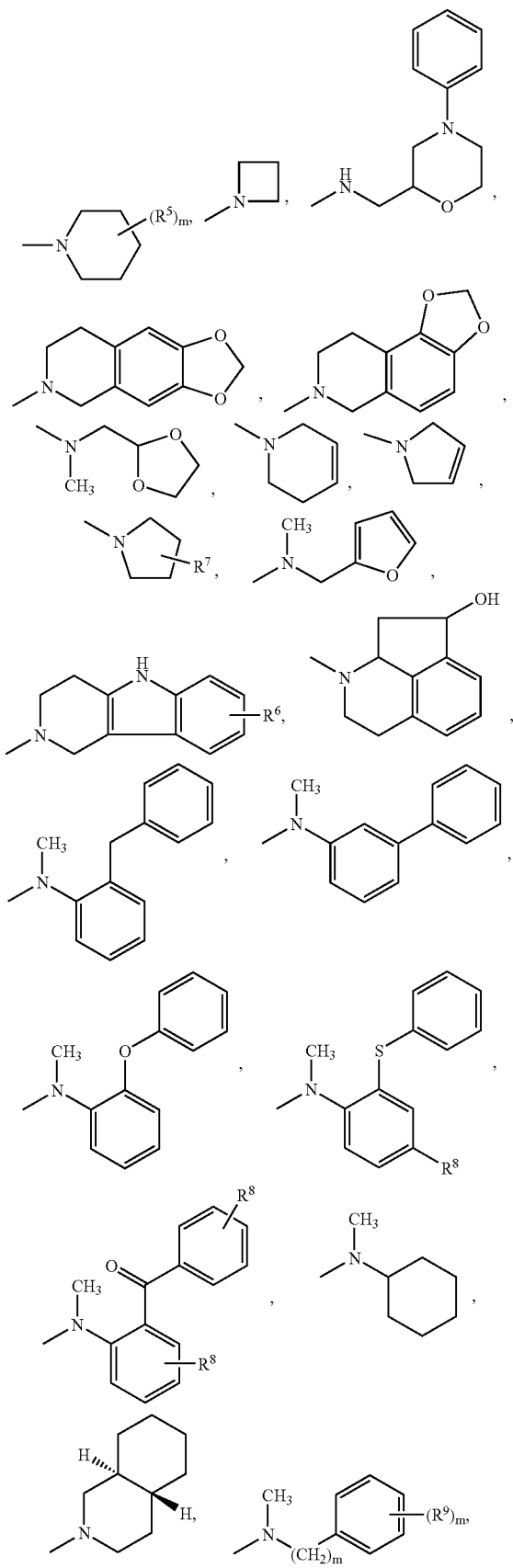
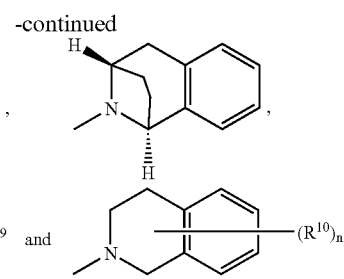
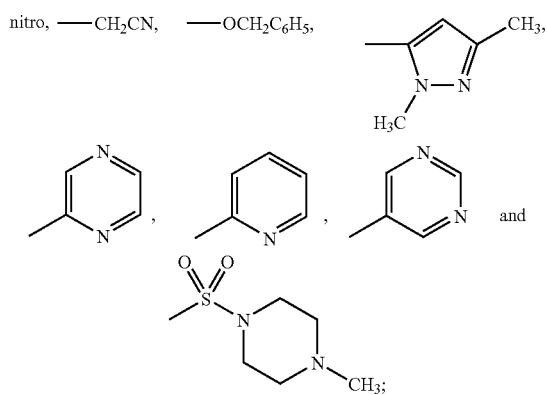

wherein
each $R^5$ is independently selected from the group consisting of hydrogen, halogen, lower alkyl and —$(CH_2)_m OH$;
$R^6$ is hydrogen, halogen or lower alkoxy;
$R^7$ is hydrogen or —$CH_2 OCH_3$;
$R^8$ is hydrogen or halogen;
$R^9$ is hydrogen, lower alkoxy, lower alkyl or amino;
each $R^{10}$ is independently selected from the group consisting of hydrogen, lower alkyl, lower alkoxy, lower cycloalkyl, halogen, hydroxy, =O, amino, nitro, —$CH_2CN$, —$OCH_2C_6H_5$,

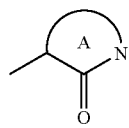

m is 1 or 2;
n is 1, 2 or 3;

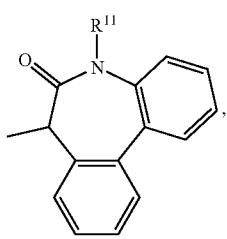

is selected from the group consisting of a)

-continued b) 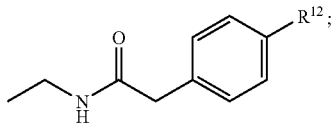

or a pharmaceutically acceptable acid addition salt thereof.

3. A compound of formula IA in accordance with claim 1.

4. A compound of formula IA in accordance with claim 3, wherein c) 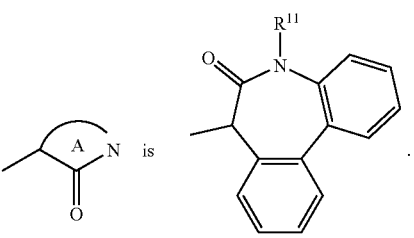

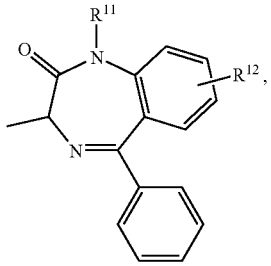

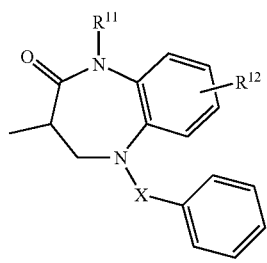

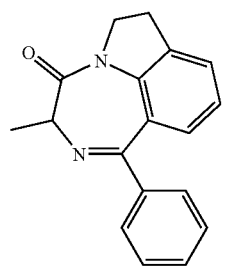

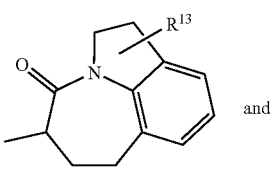

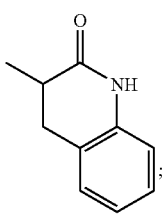

wherein
X is —CH$_2$, —S(O)$_2$ or —C(O)—;
R$^{11}$ is hydrogen or lower alkyl;
R$^{12}$ is hydrogen or halogen;
R$^{13}$ is hydrogen, CN, hydroxy, —C(O)NH$_2$,

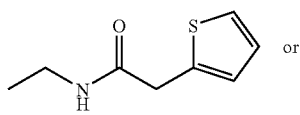

5. A compound in accordance with claim 1 selected from the group consisting of
N-(3,5-difluoro-benzyl)-2-methyl-N'-(5-methyl-6-oxo-6,7-dihydro-5H-dibenzo[b,d]azepin-7-yl)-malonamide,
N-(3,5-difluoro-benzyl)-2-fluoro-2-methyl-N'-(5-methyl-6-oxo-6,7-dihydro-5H-dibenzo[b,d]azepin-7-yl)-malonamide,
N-(3,5-difluoro-benzyl)-2-isopropyl-N'-(5-methyl-6-oxo-6,7-dihydro-5H-dibenzo[b,d]azepin-7-yl)-malonamide,
N-(3,5-difluoro-benzyl)-2-ethyl-N'-(5-methyl-6-oxo-6,7-dihydro-5H-dibenzo[b,d]azepin-7-yl)-malonamide,
N-(3,5-difluoro-benzyl)-2-fluoro-N'-(5-methyl-6-oxo-6,7-dihydro-5H-dibenzo[b,d]azepin-7-yl)-malonamide,
N-(3,5-difluoro-benzyl)-2,2-dimethyl-N'-(5-methyl-6-oxo-6,7-dihydro-5H-dibenzo[b,d]azepin-7-yl)-malonamide,
N-(3,5-difluoro-benzyl)-N'-(5-methyl-6-oxo-6,7-dihydro-5H-dibenzo[b,d]azepin-7-yl)-2-propyl-malonamide,
N-benzyl-2-methyl-N'-(5-methyl-6-oxo-6,7-dihydro-5H-dibenzo[b,d]azepin-7-yl)-malonamide,
N-(4-fluoro-benzyl)-2-methyl-N'-(5-methyl-6-oxo-6,7-dihydro-5H-dibenzo[b,d]azepin-7-yl)-malonamide,
N-(4-chloro-benzyl)-2-methyl-N'-(5-methyl-6-oxo-6,7-dihydro-5H-dibenzo[b,d]azepin-7-yl)-malonamide,
N-(3-fluoro-benzyl)-2-methyl-N'-(5-methyl-6-oxo-6,7-dihydro-5H-dibenzo[b,d]azepin-7-yl)-malonamide,
N-(2,5-difluoro-benzyl)-2-methyl-N'-(5-methyl-6-oxo-6,7-dihydro-5H-dibenzo[b,d]azepin-7-yl)-malonamide,
2-methyl-N-(5-methyl-6-oxo-6,7-dihydro-5H-dibenzo[b,d]azepin-7-yl)-N'-(2,3,5-trifluoro-benzyl)-malonamide,
N-(2-fluoro-benzyl)-2-methyl-N'-(5-methyl-6-oxo-6,7-dihydro-5H-dibenzo[b,d]azepin-7-yl)-malonamide,
N-(2-chloro-benzyl)-2-methyl-N'-(5-methyl-6-oxo-6,7-dihydro-5H-dibenzo[b,d]azepin-7-yl)-malonamide and
N-(3-chloro-benzyl)-2-methyl-N'-(5-methyl-6-oxo-6,7-dihydro-5H-dibenzo[b,d]azepin-7-yl)-malonamide.

6. A compound of formula IA in accordance with claim 3 wherein

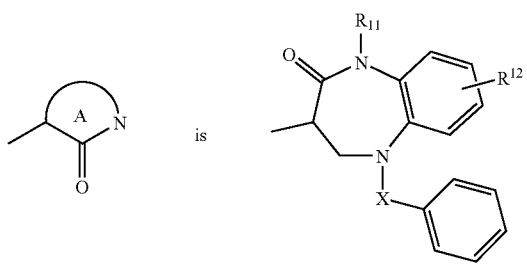

7. A compound in accordance with claim 6, selected from the group consisting of
  (N-(3,5-difluoro-benzyl)-2-methyl-N'-(1-methyl-2-oxo-5-phenyl-2,3-dihydro-1H-benzo[e][1,4]diazepin-3-yl)-malonamide,
  N-(3,5-difluoro-benzyl)-2-fluoro-2-methyl-N'-(1-methyl-2-oxo-5-phenyl-2,3-dihydro-1H-benzo[e][1,4]diazepin-3-yl)-malonamide,
  N-(3,5-difluoro-benzyl)-N'-(1-methyl-2-oxo-5-phenyl-2,3-dihydro-1H-benzo[e][1,4]diazepin-3-yl)-2-propyl-malonamide,
  N-(3,5-difluoro-benzyl)-2-ethyl-N'-(1-methyl-2-oxo-5-phenyl-2,3-dihydro-1H-benzo[e][1,4]diazepin-3-yl)-malonamide and
  N-(4-chloro-benzyl)-2-methyl-N'-(1-methyl-2-oxo-5-phenyl-2,3-dihydro-1H-benzo[e][1,4]diazepin-3-yl)-malonamide.

8. A compound of formula IA in accordance with claim 3, wherein

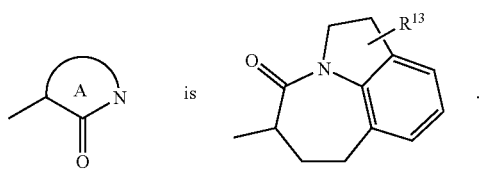

9. A compound in accordance with claim 8, selected from the group consisting of
  N-(5-benzyl-1-methyl-2-oxo-2,3,4,5-tetrahydro-1H-benzo[b][1,4]diazepin-3-yl)-N'-(3,5-difluoro-benzyl)-2-methyl-malonamide,
  N-(5-benzenesulfonyl-1-methyl-2-oxo-2,3,4,5-tetrahydro-1H-benzo[b][1,4]diazepin-3-yl)-N'-(3,5-difluoro-benzyl)-2-methyl-malonamide and
  N-(5-benzoyl-1-methyl-2-oxo-2,3,4,5-tetrahydro-1H-benzo[b][1,4]diazepin-3-yl)-N'-(3,5-difluoro-benzyl)-2-methyl-malonamide.

10. A compound of formula IA in accordance with claim 3, wherein

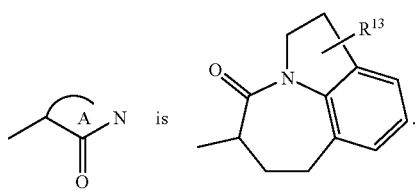

11. A compound in accordance with claim 10, selected from the group consisting of (2S-cis)-N-(3,5-difluoro-benzyl)-2-methyl-N'-{4-oxo-2-[(2-thiophen-2-yl-acetylamino)-(2R,S)-methyl]-1,2,4,5,6,7-hexahydro-azepino[3,2,1-hi]indol-5-yl}-malonamide and (2S-cis)-N-(3,5-difluoro-benzyl)-N'-(2-{[2-(4-fluoro-phenyl)-acetylamino]-methyl}-4-oxo-1,2,4,5,6,7-hexahydro-azepino[3,2,1-hi]indol-5-yl)-2,2-dimethyl-malonamide.

12. A compound of formula IB in accordance with claim 1.

13. A compound of formula IB in accordance with claim 2.

14. A compound in accordance with claim 1, wherein at least one $R^2$ is fluoro.

15. A composition comprising a compound of claim 1 and a pharmaceutically acceptable carrier.

16. A composition comprising a compound of claim 2 and a pharmaceutically acceptable carrier.

17. A process for preparing a compound of formula IA as defined in claim 1 which process comprises
reacting a compound of formula

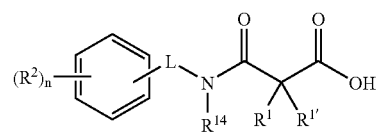

VI with a compound of formula

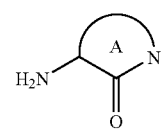

VII to produce a compound of formula

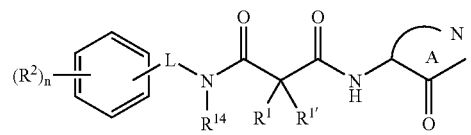

IA wherein the substituents are defined in claim 1.

18. A process for preparing a compound of formula IB as defined in claim 1 which process comprises
reacting a compound of formula

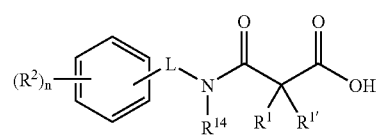

VI with a compound of formula
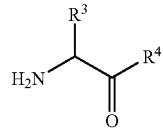
VIII
to produce a compound of formula
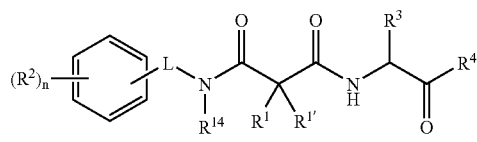
IB
wherein the substituents are defined in claim 1.
19. A process for preparing a compound of formula IA as defined in claim 1 which process comprises
reacting a compound of formula
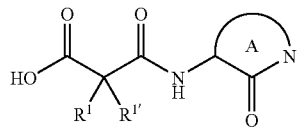
XI
with a compound of formula
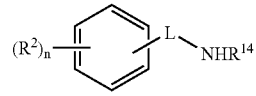
IV
to produce a compound of formula
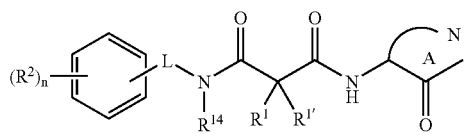
IA
wherein the substituents are defined in claim 1.
* * * * *